(12) United States Patent
Koguchi et al.

(10) Patent No.: US 10,138,312 B2
(45) Date of Patent: Nov. 27, 2018

(54) PROTEIN ADHESION INHIBITOR

(71) Applicant: ASAHI GLASS COMPANY, LIMITED, Chiyoda-ku (JP)

(72) Inventors: Ryohei Koguchi, Chiyoda-ku (JP); Kyoko Yamamoto, Chiyoda-ku (JP); Yuriko Kaida, Chiyoda-ku (JP); Tohru Itoh, Haibara-gun (JP); Aya Wada, Haibara-gun (JP); Hajime Eguchi, Yokohama (JP)

(73) Assignee: AGC Inc., Chiyoda-ku (JP)

( * ) Notice: Subject to any disclaimer, the term of this patent is extended or adjusted under 35 U.S.C. 154(b) by 18 days.

(21) Appl. No.: 15/387,280

(22) Filed: Dec. 21, 2016

(65) Prior Publication Data

US 2017/0101497 A1    Apr. 13, 2017

Related U.S. Application Data

(63) Continuation of application No. PCT/JP2015/068871, filed on Jun. 30, 2015.

(30) Foreign Application Priority Data

Jun. 30, 2014 (JP) .................................. 2014-135329
Nov. 18, 2014 (JP) .................................. 2014-233966

(51) Int. Cl.
  *C08F 220/24*      (2006.01)
  *C08F 230/02*      (2006.01)
  (Continued)

(52) U.S. Cl.
  CPC ............ *C08F 220/24* (2013.01); *A61L 27/34* (2013.01); *A61L 27/50* (2013.01); *A61L 29/085* (2013.01);
  (Continued)

(58) Field of Classification Search
  USPC .......................................... 526/242; 523/122
  See application file for complete search history.

(56) References Cited

U.S. PATENT DOCUMENTS 5,329,948 A * 7/1994 Nogi .................. A47L 15/0055
                                              134/25.2
5,427,127 A * 6/1995 Nogi .................. A47L 15/0055
                                              134/100.1

(Continued)

FOREIGN PATENT DOCUMENTS

JP          4-357917         12/1992
JP          9-241330          9/1997
                 (Continued)

OTHER PUBLICATIONS

International Search Report dated Oct. 6, 2015 in PCT/JP2015/068871, filed on Jun. 30, 2015.
(Continued)

*Primary Examiner* — Mark Kaucher
*Assistant Examiner* — Henry Hu
(74) *Attorney, Agent, or Firm* — Oblon, McClelland, Maier & Neustadt, L.L.P.

(57) ABSTRACT

To provide an inhibitor for inhibiting protein adhesion capable of easily forming a coating layer which is excellent in water resistance, from which coating components are less likely to be eluted, on which protein is less likely to be adsorbed and which is excellent in biocompatibility; a coating solution; a medical device having a coating layer employing this inhibitor for inhibiting protein adhesion; a method for producing the same; and a fluoropolymer to be used in this inhibitor for inhibiting protein adhesion. A compound for inhibiting protein adhesion comprising a fluoropolymer that has units having a biocompatible group, a fluorine atom content of from 5 to 60 mass % and a proportion P represented by the following formula of from (Continued)

0.1 to 4.5%. (Proportion P)=((proportion (mass %) of units having a biocompatible group to all units of the fluoropolymer))/(fluorine atom content (mass %) of the fluoropolymer))×100.

12 Claims, 1 Drawing Sheet

(51) Int. Cl.
| | |
|---|---|
| C08F 220/36 | (2006.01) |
| C09D 133/14 | (2006.01) |
| C09D 133/16 | (2006.01) |
| C12M 1/00 | (2006.01) |
| A61L 27/34 | (2006.01) |
| A61L 27/50 | (2006.01) |
| A61L 29/08 | (2006.01) |
| A61L 29/14 | (2006.01) |
| A61L 31/10 | (2006.01) |
| A61L 31/14 | (2006.01) |
| C12M 1/22 | (2006.01) |
| C09J 143/02 | (2006.01) |

(52) U.S. Cl.
CPC ............... *A61L 29/14* (2013.01); *A61L 31/10* (2013.01); *A61L 31/14* (2013.01); *C08F 220/36* (2013.01); *C08F 230/02* (2013.01); *C09D 133/14* (2013.01); *C09D 133/16* (2013.01); *C09J 143/02* (2013.01); *C12M 23/10* (2013.01); *C12M 23/20* (2013.01); *C08F 2220/365* (2013.01); *C08F 2800/10* (2013.01)

(56) References Cited

U.S. PATENT DOCUMENTS

| | | | | |
|---|---|---|---|---|
| 2011/0039975 | A1* | 2/2011 | Hara | C08F 220/22 523/122 |
| 2012/0309883 | A1* | 12/2012 | Inoue | C08F 220/22 524/377 |

FOREIGN PATENT DOCUMENTS

| | | |
|---|---|---|
| JP | 2000-169526 | 6/2000 |
| JP | 2007-217516 | 8/2007 |
| JP | 2007-314723 | 12/2007 |
| JP | 2011-84595 | 4/2011 |
| JP | 4774989 | 9/2011 |
| JP | 2012-77225 | 4/2012 |
| WO | WO 01/07097 A1 | 2/2001 |
| WO | WO 2009/145234 A1 | 12/2009 |
| WO | WO 2011/099534 A1 | 8/2011 |

OTHER PUBLICATIONS

Kobunshi Ronbunshu, Polymer Science and Technology, vol. 35, No. 7, Jul. 1978, pp. 5.

\* cited by examiner

PROTEIN ADHESION INHIBITOR

This application is a continuation of PCT Application No. PCT/JP2015/068871, filed on Jun. 30, 2015, which is based upon and claims the benefit of priority from Japanese Patent Application No. 2014-135329 filed on Jun. 30, 2014, and Japanese Patent Application No. 2014-233966 filed on Nov. 18, 2014. The contents of those applications are incorporated herein by reference in their entireties.

TECHNICAL FIELD

The present invention relates to a protein adhesion inhibitor, a coating solution, a medical device and a method for its production, and a fluoropolymer.

This application claims priority based on Japanese Patent Application No. 2014-135329 filed on Jun. 30, 2014, and Japanese Patent Application No. 2014-233966 filed on Nov. 18, 2014, and the entire contents of their specifications, claims, drawings and abstracts are incorporated by reference as disclosure in the specification of the present invention.

BACKGROUND ART

Synthetic polymer materials such as hydrophobic polymers (polyvinyl chloride, polystyrene, silicone resin, polymethacrylic acid ester, fluororesin, etc.) and hydrophilic polymers (polyvinyl alcohol, poly (2-hydroxyethyl methacrylate), polyacrylamide, etc.), etc. are widely used as medical polymer materials. For example, medical devices, such as cell culture vessels, catheters or artificial organs are known wherein such synthetic polymer materials are used as medical polymer materials.

However, the above synthetic polymer materials are insufficient in biocompatibility. That is, a protein such as fibrinogen, immunoglobulin G (IgG), insulin, histone, carbonic anhydrase, etc. is likely to be easily adsorbed on the device surface. Once the protein is adsorbed on the device surface, further cells (blood cells, platelets, etc.) are likely to adhere at that portion. Therefore, adverse effects on the living body such as thrombus formation, inflammatory reaction, etc. or problems such as deterioration of the device are likely to be brought about.

Therefore, in the medical device using a synthetic polymer material, it has been attempted to improve the biocompatibility by forming, on its surface, a coating layer made of a synthetic polymer material such as a polymer of 2-methacryloyloxyethyl phosphorylcholine having a structure similar to a biological membrane, or a polymer containing polyoxyethylene glycol (e.g. Non-Patent Document 1).

However, the above synthetic polymer material is water soluble, and therefore, if the coating layer is formed by the synthetic polymer material alone, the synthetic polymer material tends to elute from the coating layer during use of the device, and the biocompatibility tends to be reduced. Therefore, it has been proposed to increase the water resistance e.g. by copolymerizing the above 2-methacryloyloxyethyl phosphorylcholine with a hydrophobic monomer such as butyl methacrylate (Patent Document 1), by reacting a prepolymer having a hydroxy group and a phospholipid-like structure with a diisocyanate compound thereby to crosslink them by a urethane bond (Patent Document 2), or by fixing a hydrophilic polymer obtained by copolymerizing an epoxy group-containing monomer, on the surface of a material by the reaction of epoxy groups (Patent Document 3).

PRIOR ART DOCUMENTS

Patent Documents

Patent Document 1: Japanese Patent No. 4,774,989
Patent Document 2: JP-A-9-241330
Patent Document 3: WO2001/007097

Non-Patent Document

Non-Patent Document 1: Polymer Science and Technology Vol. 35, No. 7, pp. 423-427, 1978

DISCLOSURE OF INVENTION

Technical Problem

However, it is difficult to obtain sufficient water resistance by the method of copolymerizing with a hydrophobic monomer, as disclosed in Patent Document 1.

Further, by the method of using a diisocyanate compound or an epoxy group-containing monomer, as disclosed in Patent Documents 2 and 3, the process becomes complicated.

An object of the present invention is to provide a protein adhesion inhibitor and a coating solution capable of easily forming a coating layer which is excellent in water resistance, from which coating components are less likely to be eluted, on which protein is less likely to be adsorbed and which is excellent in biocompatibility. Further, another object of the present invention is to provide a medical device having a coating layer employing such a protein adhesion inhibitor and a method for its production, as well as a fluoropolymer to be used in such a protein adhesion inhibitor.

Solution to Problem

The present invention has the following constructions [1] to [15].

[1] A protein adhesion inhibitor comprising a fluoropolymer having units having a biocompatible group, a fluorine atom content of from 5 to 60 mass % and a proportion P represented by the following formula of from 0.1 to 4.5%:

(Proportion $P$)=[(proportion (mass %) of units having a biocompatible group to all units of the fluoropolymer)/(fluorine atom content (mass %) of the fluoropolymer)]×100.

[2] The protein adhesion inhibitor according to the above [1], wherein the biocompatible group is at least one member selected from the group consisting of a group represented by the following formula (1), a group represented by the following formula (2) and a group represented by the following formula (3):

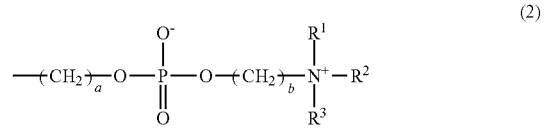

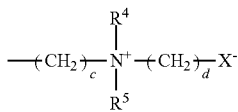
(3)

(in the formulae, n is an integer of from 1 to 10, m is an integer of from 1 to 100 in a case where the group represented by the formula (1) is contained in a side chain in the fluoropolymer, or from 5 to 300 in a case where contained in the main chain, $R^1$ to $R^3$ are each independently a $C_{1-5}$ alkyl group, a is an integer of from 1 to 5, b is an integer of from 1 to 5, $R^4$ and $R^5$ are each independently a $C_{1-5}$ alkyl group, $X^-$ is a group represented by the following formula (3-1) or a group represented by the following formula (3-2), c is an integer of from 1 to 20, and d is an integer of from 1 to 5),

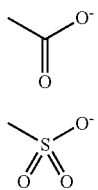
(3-1)

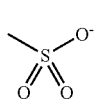
(3-2)

[3] The protein adhesion inhibitor according to the above [1] or [2], wherein the fluoropolymer has units (m1) derived from a monomer represented by the following formula (m1), and at least one member selected from the group consisting of units (m2) derived from a monomer represented by the following formula (m2) and units (m3) derived from a monomer represented by the following formula (m3):

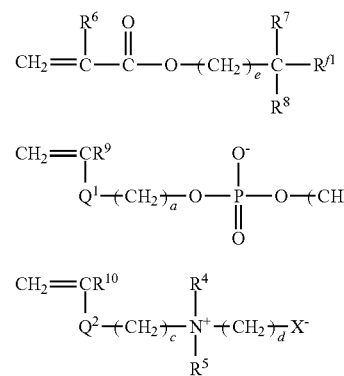
(m1)

(m2)

(m3)

(in the above formulae, $R^6$ is a hydrogen atom, a chlorine atom or a methyl group, e is an integer of from 0 to 3, $R^7$ and $R^8$ are each independently a hydrogen atom, a fluorine atom or a trifluoromethyl group, $R^{f1}$ is a $C_{1-20}$ perfluoroalkyl group, $R^9$ is a hydrogen atom, a chlorine atom or a methyl group, $Q^1$ is —C(=O)—O— or —C(=O)—NH—, $R^1$ to $R^3$ are each independently a $C_{1-5}$ alkyl group, a is an integer of from 1 to 5, b is an integer of from 1 to 5, $R^{10}$ is a hydrogen atom, a chlorine atom or a methyl group, $Q^2$ is —C(=O)—O— or —C(=O)—NH—, $R^4$ and $R^5$ are each independently a $C_{1-5}$ alkyl group, $X^-$ is a group represented by the following formula (3-1) or a group represented by the following formula (3-2), c is an integer of from 1 to 20, and d is an integer of from 1 to 5),

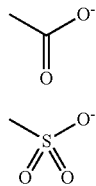
(3-1)

(3-2)

[4] The protein adhesion inhibitor according to the above [1] or [2], wherein the fluoropolymer has units (m1) derived from a monomer represented by the following formula (m1) and units (m4) derived from a monomer represented by the following formula (m4):

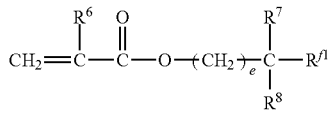
(m1)

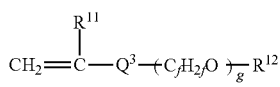
(m4)

(in the above formulae, $R^6$ is a hydrogen atom, a chlorine atom or a methyl group, e is an integer of from 0 to 3, $R^7$ and $R^8$ are each independently a hydrogen atom, a fluorine atom or a trifluoromethyl group, $R^{f1}$ is a $C_{1-20}$ perfluoroalkyl group, $R^{11}$ is a hydrogen atom, a chlorine atom or a methyl group, $Q^3$ is —COO— or —COO(CH$_2$)$_h$—NHCOO— (wherein h is an integer of from 1 to 4), $R^{12}$ is a hydrogen atom or —(CH$_2$)$_i$—$R^{13}$ (wherein $R^{13}$ is a $C_{1-8}$ alkoxy group, a hydrogen atom, a fluorine atom, a trifluoromethyl group or a cyano group, i is an integer of from 1 to 25), f is an integer of from 1 to 10, and g is an integer of from 1 to 100).

[5] The protein adhesion inhibitor according to the above [1] or [2], wherein the fluoropolymer has a segment (I) comprising units (m6) derived from a monomer represented by the following formula (m6), and a segment (II) comprising a molecular chain derived from a polymeric azo initiator having a structure represented by the following formula (6):

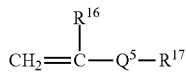
(m6)

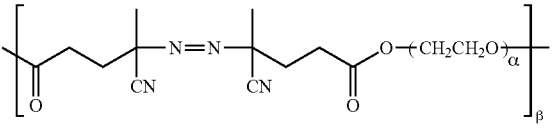
(6)

(in the above formulae, $R^{16}$ is a hydrogen atom, a $C_{1-4}$ alkyl group or a halogen atom, $Q^5$ is a single bond or a divalent organic group, $R^{17}$ is a $C_{1-6}$ polyfluoroalkyl group which may have an etheric oxygen atom between carbon atoms, α is an integer of from 5 to 300, and β is an integer of from 1 to 20).

[6] Use of a fluoropolymer having units having a biocompatible group, a fluorine atom content of from 5 to 60 mass % and a proportion P represented by the following formula of from 0.1 to 4.5%, for prevention of protein adhesion to a medical device:

(Proportion $P$)=[(proportion (mass %) of units having a biocompatible group to all units of the fluoropolymer)/(fluorine atom content (mass %) of the fluoropolymer)]×100.

[7] A coating solution comprising the protein adhesion inhibitor as defined in any one of the above [1] to [5] and a solvent.
[8] The coating solution according to the above [7], which further contains a crosslinking agent.
[9] The coating solution according to the above [8], wherein the fluoropolymer contained in the protein adhesion inhibitor as defined in any one of the above [1] to [5] has a hydroxy group, and the above crosslinking agent is a polyfunctional isocyanate compound.
[10] Use of a coating solution comprising a fluoropolymer having units having a biocompatible group, a fluorine atom content of from 5 to 60 mass % and a proportion P represented by the following formula of from 0.1 to 4.5%, and a solvent, for prevention of protein adhesion to a medical device:

(Proportion $P$)=[(proportion (mass %) of units having a biocompatible group to all units of the fluoropolymer)/(fluorine atom content (mass %) of the fluoropolymer)]×100.

[11] A medical device comprising a device substrate and a coating layer formed on the device substrate, wherein the coating layer is a layer formed from the protein adhesion inhibitor as defined in any one of the above [1] to [5].
[12] The medical device according to the above [11], which is a cell culture vessel.
[13] A method for producing a medical device, which comprises a coating step of applying the coating solution as defined in the above 8 or 9 onto a device substrate and a drying step of removing the solvent derived from the coating solution to obtain a medical device having a coating layer formed on the device substrate.
[14] A fluoropolymer having units (m1) derived from a monomer represented by the following formula (m1) and units (m41) derived from a monomer represented by the following formula (m41):

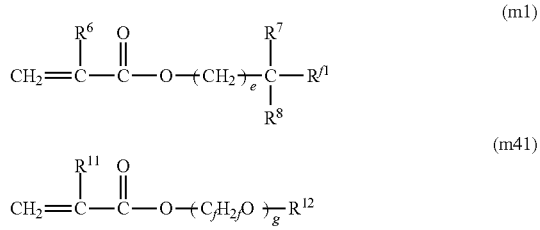

(in the above formulae, $R^6$ is a hydrogen atom, a chlorine atom or a methyl group, e is an integer of from 0 to 3, $R^7$ and $R^8$ are each independently a hydrogen atom, a fluorine atom or a trifluoromethyl group, $R^{f1}$ is a $C_{1-20}$ perfluoroalkyl group, $R^{11}$ is a hydrogen atom, a chlorine atom or a methyl group, $R^{12}$ is a hydrogen atom or —$(CH_2)_i$—$R^{13}$ (wherein $R^{13}$ is a $C_{1-8}$ alkoxy group, a hydrogen atom, a fluorine atom, a trifluoromethyl group or a cyano group, and i is an integer of from 1 to 25), f is an integer of from 1 to 10, and g is an integer of from 1 to 100).

[15] A fluoropolymer having a segment (I) comprising units (m6) derived from a monomer represented by the following formula (m6) and a segment (II) comprising a molecular chain derived from a polymeric azo initiator having a structure represented by the following formula (6):

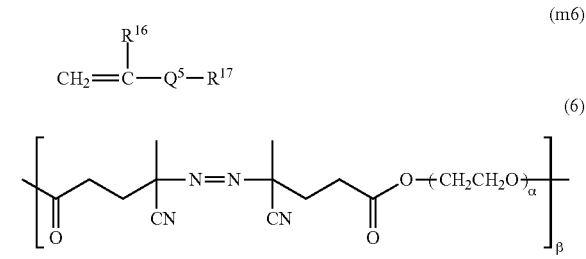

(in the above formulae, $R^{16}$ is a hydrogen atom, a chlorine atom or a methyl group, $Q^5$ is a single bond or a divalent organic group, $R^{17}$ is a $C_{1-6}$ polyfluoroalkyl group which may have an etheric oxygen atom between carbon atoms, α is an integer of from 5 to 300, and β is an integer of from 1 to 20).

Advantageous Effects of Invention

The protein adhesion inhibitor and the coating solution of the present invention, are capable of easily forming a coating layer which is excellent in water resistance, from which coating components are less likely to be eluted, on which protein is less likely to be adsorbed and which is excellent in biocompatibility.

Further, the medical device of the present invention has a coating layer which is excellent in water resistance, from which coating components are less likely to be eluted, on which protein is less likely to be adsorbed and which is excellent in biocompatibility.

Further, the fluoropolymer of the present invention is capable of easily forming a coating layer which is excellent in water resistance, from which coating components are less likely to be eluted, on which protein is less likely to be adsorbed and which is excellent in biocompatibility.

DESCRIPTION OF EMBODIMENTS

Figure 1:
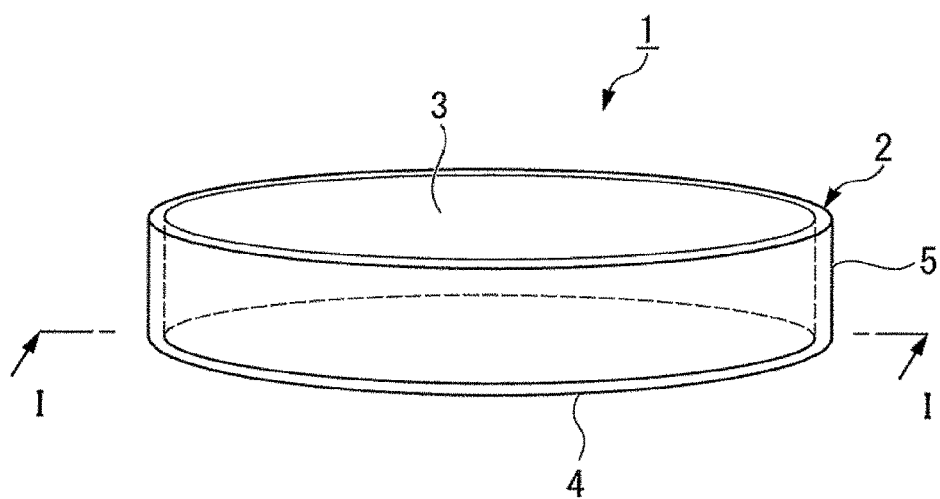
FIG. 1 is a perspective view showing an example of a medical device of the present invention.

The following definitions of terms apply throughout the present specification including claims.

A "fluoropolymer" means a polymer compound having fluorine atom(s) in the molecule.

A "glass transition temperature (Tg)" of a polymer means a temperature for a change from the rubbery state to the glass state, as measured by a differential scanning calorimetry (DSC) method.

A "unit" means a moiety derived from a monomer, which is present in a polymer and which constitutes the polymer.

A unit derived from a monomer having a carbon-carbon unsaturated double bond, formed by addition polymerization of the monomer, is a divalent unit formed by cleavage of the unsaturated double bond. Further, one obtained by chemically converting the structure of a certain unit after formation of a polymer will also be referred to as a unit. In the following, in some cases, a unit derived from an individual monomer may be referred to by a name having "unit" attached to the monomer's name.

A "(meth)acrylate" is a generic term for an acrylate and a methacrylate.

A "biocompatible group" means a group having a property of inhibiting adsorption of protein on a polymer and adhesion and fixing of cells on a polymer.

A "segment" means a molecular chain formed by two or more units which are chained.

The term "biocompatibility" means a property not to let protein be adsorbed, or not to let cells be adhered.

A "medical device" is a device used for a medical purpose such as therapeutic, diagnostic, anatomical or biological examination, and includes a device to be inserted or contacted with a living body such as a human body, or to be in contact with a medium (such as blood) taken out from a living body.

A "cell" is the most fundamental unit constituting a living body and means one which has, in the interior of the cell membrane, the cytoplasm and various organelles. Nuclei containing DNA may be contained or may not be contained inside the cell.

Animal-derived cells include germ cells (sperm, ova, etc.), somatic cells constituting a living body, stem cells, progenitor cells, cancer cells separated from a living body, cells (cell line) which are separated from a living body and have won immortalized ability and thus are stably maintained outside the body, cells separated from a living body and artificially genetically engineered, cells separated from a living body and having nuclei artificially replaced, etc.

Somatic cells constituting a living body include fibroblasts, bone marrow cells, B lymphocytes, T lymphocytes, neutrophils, erythrocytes, platelets, macrophages, monocytes, bone cells, bone marrow cells, pericytes, dendritic cells, keratinocytes, fat cells, mesenchymal cells, epithelial cells, epidermal cells, endothelial cells, vascular endothelial cells, hepatocytes, cartilage cells, cumulus cells, neural cells, glial cells, neurons, oligodendrocytes, microglia, astrocytes, cardiac cells, esophagus cells, muscle cells (for example, smooth muscle cells, skeletal muscle cells), pancreatic beta cells, melanin cells, hematopoietic progenitor cells, mononuclear cells, etc.

The somatic cells include cells taken from optional tissues, such as skin, kidneys, spleen, adrenal gland, liver, lung, ovary, pancreas, uterus, stomach, colon, small intestine, large intestine, bladder, prostate, testis, thymus, muscle, connective tissue, bone, cartilage, vascular tissue, blood, heart, eye, brain, nervous tissue, etc.

The stem cells are cells having both an ability to replicate themselves and an ability to be differentiated into cells of other multiple systems, and include embryonic stem cells (ES cells), embryonic carcinoma cells, embryonic germ stem cells, induced pluripotent stem cells (iPS cells), neural stem cells, hematopoietic stem cells, mesenchymal stem cells, liver stem cells, pancreatic stem cells, muscle stem cells, germ stem cells, intestinal stem cells, cancer stem cells, hair follicle stem cells, etc.

The progenitor cells are cells at an intermediate stage during differentiation into specific somatic or germ cells from the stem cells.

The cancer cells are cells that have acquired an unlimited proliferative capacity as derived from somatic cells.

A cell line is cells which have acquired an unlimited proliferative capacity by an artificial manipulation in vitro, and includes HCT116, Huh7, HEK293 (human embryonic kidney cells), HeLa (human cervical carcinoma cell line), HepG2 (human liver cancer cell line), UT7/TPO (human leukemia cell line), CHO (Chinese hamster ovary cell line), MDCK, MDBK, BHK, C-33A, HT-29, AE-1, 3D9, Ns0/1, Jurkat, NIH3T3, PC12, S2, Sf9, Sf21, High Five, Vero, etc.

In the present specification, a group represented by the formula (1) will be referred to as a group (1). Groups represented by other formulae will be referred to in the same manner.

[Protein Adhesion Inhibitor]

The protein adhesion inhibitor of the present invention is an agent to form a coating layer to prevent adsorption of at least one type of protein selected from the group consisting of fibrinogen, immunoglobulin G (IgG), insulin, histones and carbonic anhydrase on the surface of a medical device. By preventing adsorption of the protein, it is possible to further prevent adhesion of cells to the protein.

The protein adhesion inhibitor of the present invention is made of a fluoropolymer which has units having a biocompatible group and a proportion P to be described later of from 0.1 to 4.5%.

(Fluoropolymer)

The fluoropolymer in the present invention (hereinafter referred to also as "fluoropolymer (A)") is a fluoropolymer which has units having a biocompatible group, a fluorine atom content of 5 to 60 mass % and a proportion P represented by the following formula of 0.1 to 4.5%. The fluoropolymer (A) is useful, for example, for preventing adhesion of protein to a medical device. Specifically, by a medical device provided with a coating layer formed of the fluoropolymer (A), it is possible to prevent adhesion of protein to the medical device.

(Proportion $P$)=[(proportion (mass %) of units having a biocompatible group to all units of the fluoropolymer $(A)$)/(fluorine atom content (mass %) of the fluoropolymer $(A)$)]×100

<Biocompatible Group>

The biocompatible group is preferably at least one member selected from the group consisting of the following group (1), group (2) and group (3), from such a viewpoint that it is thereby easy to form a coating layer whereby the effect to prevent adsorption of protein is high. As the biocompatible group, from such a viewpoint that it is thereby easy to obtain the effect to prevent adsorption of protein, preferred is the group (1) only, or one or both of the group (2) and the group (3), and particularly preferred is either one of the group (1), the group (2) or the group (3). The fluoropolymer (A) is excellent in biocompatibility when it contains any of the groups (1) to (3).

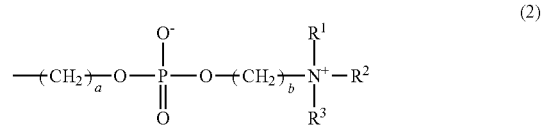

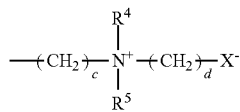

Here, in the above formulae, n is an integer of from 1 to 10, m is an integer of from 1 to 100 in a case where the group (1) is contained in a side chain in the fluoropolymer (A) or from 5 to 300 in a case where contained in the main chain, $R^1$ to $R^3$ are each independently a $C_{1-5}$ alkyl group, a is an integer of from 1 to 5, b is an integer from 1 to 5, $R^4$ and $R^5$ are each independently a $C_{1-5}$ alkyl group, $X^-$ is the following group (3-1) or the following group (3-2), c is an integer of from 1 to 20, d is an integer of from 1 to 5.

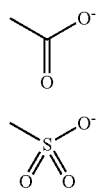

Group (1):

The group (1) has a high mobility in blood, etc., whereby protein to be adsorbed on the surface of the coating layer is less likely to be adsorbed.

The group (1) may be contained in the main chain of the fluoropolymer (A), or it may be contained in a side chain.

n in the group (1) is preferably an integer of from 1 to 6, more preferably an integer of from 1 to 4, from such a viewpoint that protein is thereby less likely to be adsorbed.

The group (1) may be linear or branched. From the viewpoint of a higher effect to prevent adsorption of protein, the group (1) is preferably linear.

When the group (1) is contained in a side chain of the fluoropolymer (A), m in the group (1) is preferably from 1 to 40, particularly from 1 to 20, from the viewpoint of excellent water resistance.

When the group (1) is contained in the main chain of the fluoropolymer (A), m in the group (1) is preferably from 5 to 300, particularly preferably from 10 to 200, from the viewpoint of excellent water resistance.

When m is 2 or more, the plurality of $(C_nH_{2n}O)$ in the group (1) may be of one type, or may be of two or more types. Further, in the case of two or more types, their disposition may be either random, block or alternating. When n is 3 or more, $(C_nH_{2n}O)$ may be a straight-chain structure or a branched structure.

In a case where the fluoropolymer (A) has groups (1), the groups (1) in the fluoropolymer (A) may be of one type, or of two or more types.

Group (2):

The group (2) has a strong affinity for phospholipids in blood, while its interaction force against plasma proteins is weak. Therefore, by using a fluoropolymer (A) having groups (2), for example, it is considered that in blood, phospholipids are adsorbed preferentially on the coating layer, and such phospholipids will be self-assembled to form an adsorption layer. As a result, since the surface becomes a structure similar to the vascular endothelial surface, adsorption of proteins, such as fibrinogen, etc., will be suppressed.

The group (2) is preferably contained in a side chain of the fluoropolymer (A).

$R^1$ to $R^3$ in the group (2) are each independently a $C_{1-5}$ alkyl group, and from the viewpoint of easy availability of raw material, preferably a $C_{1-4}$ alkyl group, particularly preferably a methyl group.

a in the group (2) is an integer of from 1 to 5, and from the viewpoint of easy availability of raw material, preferably an integer of 2 to 5, particularly preferably 2.

b in the group (2) is an integer of 1 to 5, and from such a viewpoint that protein is less likely to be adsorbed, preferably an integer of 1 to 4, particularly preferably 2.

In a case where the fluoropolymer (A) has groups (2), the groups (2) in the fluoropolymer (A) may be of one type, or of two or more types.

Group (3):

By using a fluoropolymer (A) having groups (3), adsorption of proteins is inhibited for the same reason as in the case of using the fluoropolymer (A) having groups (2).

The group (3) is preferably contained in a side chain of the fluoropolymer (A).

$R^4$ and $R^5$ in the group (3) are each independently a $C_{1-5}$ alkyl group, and from such a viewpoint that protein is less likely to be adsorbed, preferably a $C_{1-4}$ alkyl group, particularly preferably a methyl group.

c in the group (3) is an integer of from 1 to 20, and from such a viewpoint that the fluoropolymer (A) will be excellent in flexibility, preferably an integer of from 1 to 15, more preferably an integer of from 1 to 10, particularly preferably 2.

d in the group (3) is an integer of from 1 to 5, and from such a viewpoint that protein is less likely to be adsorbed, preferably an integer of from 1 to 4, particularly preferably 1.

In a case where the fluoropolymer (A) has groups (3), the groups (3) in the fluoropolymer (A) may be of one type, or of two or more types.

Further, in a case where the fluoropolymer (A) has groups (3), from such a viewpoint that protein is less likely to be adsorbed, it is preferred that the fluoropolymer (A) has either groups (3) wherein $X^-$ is a group (3-1), or groups (3) wherein $X^-$ is a group (3-2).

<Physical Properties of Fluoropolymer (A)>

The proportion P of the fluoropolymer (A) is from 0.1 to 4.5%. When the proportion P is at least the above lower limit value, it is possible to form a coating layer excellent in biocompatibility, on which protein is less likely to be adsorbed. When the proportion P is at most the above upper limit value, it is possible to form a coating layer excellent in water resistance, whereby the fluoropolymer (A) is less likely to elute in blood, etc.

The proportion P is preferably from 0.2 to 4.5%.

Here, the proportion P can be measured by the method described in Examples. Further, it can also be calculated from the charged amounts of the monomers and initiator used in the production of the fluoropolymer (A).

The fluorine atom content of the fluoropolymer (A) is from 5 to 60 mass %. The fluorine atom content is preferably from 5 to 55 mass %, particularly preferably from 5 to 50 mass %. When the fluorine atom content is at least the above lower limit value, water resistance will be excellent. When the fluorine atom content is at most the above upper limit value, protein will be less likely to be adsorbed.

Here, the fluorine atom content (mass %) is determined by the following formula.

$$(\text{Fluorine atom content})=[19 \times N_F/M_A] \times 100$$

$N_F$: the sum of values obtained by multiplying, for every type of units that constitute the fluoropolymer, the number of fluorine atoms in the unit by the molar ratio of the unit to all units.

$M_A$: the sum of values obtained by multiplying, for every type of units that constitute the fluoropolymer, the total atomic weight of all atoms constituting the unit by the molar ratio of the unit to all units.

As a specific example, the fluorine atom content of a fluoropolymer having 50 mol % of tetrafluoroethylene (TFE) units and 50 mol % of ethylene (E) units, will be described as follows.

In the case of such a fluoropolymer, the value obtained by multiplying the number of fluorine atoms (4) in a TFE unit by the molar ratio (0.5) of the TFE unit to all units, is 2, and the value obtained by multiplying the number of fluorine atoms (0) in an E unit by the molar ratio (0.5) of the E unit, is 0, and therefore, $N_F$ becomes to be 2. Further, the value obtained by multiplying the total atomic weight (100) of all atoms constituting the TFE unit, by the molar ratio (0.5) of the TFE unit to all units, is 50, and the value obtained by multiplying the total atomic weight (28) of all atoms constituting the E unit, by the molar ratio (0.5) of the E unit to all units, is 14, and therefore, $M_A$ becomes to be 64. Accordingly, the fluorine atom content of the fluoropolymer becomes to be 59.4 mass %.

Further, the fluorine atom content can be measured by the method described in Examples. It can also be calculated from the charged amounts of the monomers and initiator used in the production of the fluoropolymer (A).

The number-average molecular weight (Mn) of the fluoropolymer (A) is preferably from 2,000 to 1,000,000, particularly preferably from 2,000 to 800,000. When the number average molecular weight of the fluoropolymer (A) is at least the above lower limit value, durability will be excellent. When the number-average molecular weight of the fluoropolymer (A) is at most the above upper limit value, processability will be excellent.

The mass average molecular weight (Mw) of the fluoropolymer (A) is preferably from 2,000 to 2,000,000, particularly preferably from 2,000 to 1,000,000. When the mass average molecular weight of the fluoropolymer (A) is at least the above lower limit value, durability will be excellent. When the mass average molecular weight of the fluoropolymer (A) is at most the above upper limit value, processability will be excellent.

The molecular weight distribution (Mw/Mn) of the fluoropolymer (A) is preferably from 1 to 10, particularly preferably from 1.1 to 5. When the molecular weight distribution of the fluoropolymer (A) is within the above range, water resistance will be excellent, and protein will be less likely to be adsorbed.

As the fluoropolymer (A), a commercially available product may be used. Commercially available products may, for example, be the following.

Manufactured by 3M, Novec series:
FC-4430 (nonionic, containing perfluorobutane sulfonic acid groups, surface tension: 21 mN/m),
FC-4432 (nonionic, containing perfluorobutane sulfonic acid groups, surface tension: 21 mN/m), etc.

Manufactured by AGC Seimi Chemical Co., Ltd., Surflon series:
S-241 (nonionic, containing $C_{1-6}$ perfluoroalkyl groups, surface tension: 16.2 mN/m),
S-242 (nonionic, $C_{1-6}$ perfluoroalkyl group-containing ethylene oxide adduct, surface tension: 22.9 mN/m),
S-243 (nonionic, $C_{1-6}$ perfluoroalkyl group-containing ethylene oxide adduct, surface tension: 23.2 mN/m),
S-420 (nonionic, $C_{1-6}$ perfluoroalkyl group-containing ethylene oxide adduct, surface tension: 23.1 mN/m),
S-611 (nonionic, $C_{1-6}$ perfluoroalkyl group-containing polymer, surface tension: 18.4 mN/m),
S-651 (nonionic, $C_{1-6}$ perfluoroalkyl group-containing polymer, surface tension: 23.0 mN/m),
S-650 (nonionic, $C_{1-6}$ perfluoroalkyl group-containing polymer), etc.

Manufactured by DIC Corporation, MEGFAC series:
F-444 (nonionic, perfluoroalkyl ethylene oxide adduct, surface tension: 16.8 mN/m), etc.

Manufactured by Asahi Glass Company, Limited, Asahi Guard series:
E100, etc.

<Preferred Fluoropolymer (A)>

As the fluoropolymer (A), fluoropolymers (A1) to (A3) as described below are preferred from such a viewpoint that it is thereby possible to easily form a coating layer which is excellent in water resistance, from which coating components are less likely to be eluted, on which protein is less likely to be adsorbed, and which is excellent in biocompatibility. The fluoropolymers (A1) and (A2) are fluoropolymers (A) having biocompatible groups only in side chains, and the fluoropolymer (A3) is a fluoropolymer (A) having biocompatible groups in at least the main chain.

«Fluoropolymer (A1)»

The fluoropolymer (A1) is a fluoropolymer having units (hereinafter referred to also as units (m1)) derived from the following monomer (m1) and at least one member selected from the group consisting of units (hereinafter referred to also as units (m2)) derived from the monomer (m2) and units (hereinafter referred to also as unit (m3)) derived from the monomer (m3).

Monomer (m1): a monomer represented by the following formula (m1),
Monomer (m2): a monomer represented by the following formula (m2),
Monomer (m3): a monomer represented by the following formula (m3).

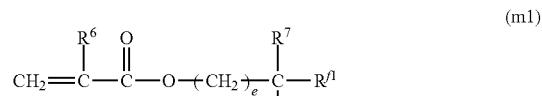

(m1)

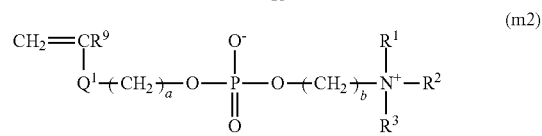

(m2)

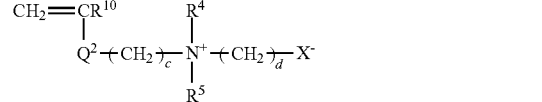

(m3)

Here, in the above formulae, $R^6$ is a hydrogen atom, a chlorine atom or a methyl group, e is an integer of from 0 to 3, $R^7$ and $R^8$ are each independently a hydrogen atom, a fluorine atom or a trifluoromethyl a group, $R^{f1}$ is a $C_{1-20}$ perfluoroalkyl group, $R^9$ is a hydrogen atom, a chlorine atom or a methyl group, $Q^1$ is —C(=O)—O— or —C(=O)—NH—, $R^1$ to $R^3$ are each independently a $C_{1-5}$ alkyl group, a is an integer of from 1 to 5, b is an integer of from 1 to 5, $R^{10}$ is a hydrogen atom, a chlorine atom or a methyl group, $Q^2$ is —C(=O)—O— or —C(=O)—NH—, $R^4$ and $R^5$ are each independently a $C_{1-5}$ alkyl group, $X^-$ is the group (3-1) or the group (3-2), c is an integer of from 1 to 20, d is an integer of from 1 to 5.

Monomer (m1):

In the formula (m1), $R^6$ is preferably a hydrogen atom or a methyl group from the viewpoint of polymerization efficiency.

e is, from the viewpoint of excellent flexibility of the fluoropolymer (A1), preferably an integer of from 1 to 3, particularly preferably 1 or 2.

$R^7$ and $R^8$ are, from the viewpoint of excellent water resistance, each preferably a fluorine atom.

The perfluoroalkyl group for $R^{f1}$ may be linear or branched. As $R^{f1}$, from the viewpoint of easy availability of raw material, a $C_{1-10}$ perfluoroalkyl group is preferred, and a $C_{1-5}$ perfluoroalkyl group is particularly preferred.

Specific examples of the monomer (m1) may, for example, be the following compounds.

$CH_2=C(CH_3)COO(CH_2)_2(CF_2)_5CF_3$,
$CH_2=CHCOO(CH_2)_2(CF_2)_5CF_3$,
$CH_2=C(CH_3)COOCH_2CF_3$,
$CH_2=CHCOOCH_2CF_3$,
$CH_2=CR^6COO(CH_2)_eCF_2CF_2CF_3$,
$CH_2=CR^6COO(CH_2)_eCF_2CF(CF_3)_2$,
$CH_2=CR^6COOCH(CF_3)_2$,
$CH_2=CR^6COOC(CF_3)_3$, etc.

As the monomer (m1), from the viewpoint of excellent water resistance, $CH_2=C(CH_3)COO(CH_2)_2(CF_2)_5CF_3$, $CH_2=CHCOO(CH_2)_2(CF_2)_5CF_3$ or $CH_2=CCH_3COOCH_2CF_3$ is particularly preferred.

Units (m1) may be of one type, or of two or more types.

Monomer (m2):

The monomer (m2) is a monomer having a group (2).

In the formula (m2), $R^9$ is preferably a hydrogen atom or a methyl group from the viewpoint of polymerization efficiency.

$Q^1$ is —C(=O)—O— or —C(=O)—NH—, and from such a viewpoint that protein is less likely to be adsorbed, —C(=O)—O— is preferred.

$R^1$ to $R^3$ are each independently a $C_{1-5}$ alkyl group, and from such a viewpoint that protein is less likely to be adsorbed, a $C_{1-4}$ alkyl group is preferred, and a methyl group is particularly preferred.

a is an integer of from 1 to 5, and from the viewpoint of excellent flexibility of the fluoropolymer (A1), it is preferably an integer of from 1 to 4, particularly preferably 2.

b is an integer of from 1 to 5, and from such a viewpoint that protein is less likely to be adsorbed, it is preferably an integer of from 1 to 4, particularly preferably 2.

Specific examples of the monomer (m2) may, for example, be 2-methacryloyloxyethyl phosphorylcholine, 2-acryloyloxyethyl phosphorylcholine, etc.

In a case where the fluoropolymer (A1) has units (m2), the units (m2) may be of one type, or of two or more types.

Monomer (m3):

The monomer (m3) is a monomer having a group (3).

In the formula (m3), $R^{10}$ is preferably a hydrogen atom or a methyl group from the viewpoint of polymerization efficiency.

$Q^2$ is —C(=O)—O— or —C(=O)—NH—, and from such a viewpoint that protein is less likely to be adsorbed on the fluoropolymer (A1), —C(=O)—O— is preferred.

$R^4$ and $R^5$ are each independently a $C_{1-5}$ alkyl group, and from the viewpoint of easy availability of raw material, a $C_{1-4}$ alkyl group is preferred, and a methyl group is particularly preferred.

$X^-$ is preferably the group (3-1) or the group (3-2).

c is an integer of from 1 to 20, and from the viewpoint of easy availability of raw material, it is preferably an integer of from 1 to 15, more preferably an integer of from 1 to 10, particularly preferably 2.

d is an integer of from 1 to 5, and from such a viewpoint that protein is less likely to be adsorbed, it is preferably an integer of from 1 to 4, particularly preferably 1.

Specific examples of the monomer (m3) may, for example, be the following compounds.

N-methacryloyloxyethyl-N,N-dimethyl ammonium-α-N-methyl carboxy betaine,
N-acryloyloxyethyl-N,N-dimethyl ammonium-α-N-methyl carboxy betaine,
N-methacryloyloxyethyl-N,N-dimethyl ammonium-α-N-propyl sulphoxy betaine,
N methacryloyl aminopropyl-N,N-dimethyl ammonium-α-N-propyl sulphoxy betaine, etc.

As the monomer (m3), from such a viewpoint that protein is less likely to be adsorbed, N-methacryloyloxyethyl-N,N-dimethyl ammonium-α-N-methyl carboxy betaine or N-acryloyloxyethyl-N,N-dimethyl ammonium-α-N-methyl carboxy betaine is preferred.

In a case where the fluoropolymer (A1) has units (m3), the units (m3) may be of one type, or of two or more types.

From such a viewpoint that protein is less likely to be adsorbed, it is particularly preferred that the fluoropolymer (A1) has, as units having a biocompatible group, either one of units (m2) or units (m3).

Here, the fluoropolymer (A1) may have all of units (m1), units (m2) and units (m3).

The fluoropolymer (A1) may have, in addition to units (m1) and at least one member selected from the group consisting of units (m2) and units (m3), units derived from another monomer other than for units (1), units (m2) and units (m3).

As such another monomer, from the viewpoint of excellent water resistance, the following monomer (m7) is preferred Monomer (m7): a monomer represented by the following formula (m7).

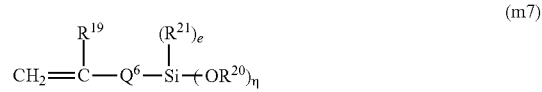

Here, $R^{19}$ is a hydrogen atom, a chlorine atom or a methyl group, $Q^6$ is —$C_6H_4$— or —C(=O)O—$(CH_2)_\rho$— (wherein ρ is an integer of from 1 to 100), and $R^{19}$ and $R^{20}$ are each independently a $C_{1-3}$ alkyl group. η is an integer of from 1 to 3, and η+θ is 3.

In the formula (m7), $R^{19}$ is, from the viewpoint of polymerization efficiency, preferably a hydrogen atom or a methyl group.

$Q^6$ is, from the viewpoint of easy availability, preferably —C(=O)O—$(CH_2)_2$—.

$R^{20}$ and $R^{21}$ are, from the viewpoint of easy availability, each independently, preferably a $C_{1-3}$ alkyl group, particularly preferably a $C_{1-2}$ alkyl group.

η is, from the viewpoint of adhesion to a substrate, preferably 2 or 3.

Specific examples of the monomer (m7) may, for example, be p-styryl trimethoxysilane, 3-methacryloyloxypropyl trimethoxy silane, 3-methacryloyloxypropylmethyl dimethoxysilane, 3-methacryloyloxypropylmethyl diethoxysilane, 3-methacryloyloxypropyl triethoxysilane, 3-acryloyloxypropyltrimethoxysilane, etc.

As the monomer (m7), 3-methacryloyloxypropyl trimethoxy silane, 3-methacryloxypropylmethyl dimethoxy silane, 3-methacryloxypropylmethyl diethoxy silane, 3-methacryloxypropyl triethoxy silane or 3-acryloxypropyl trimethoxysilane is preferred.

In a case where the fluoropolymer (A1) has units (m7) derived from a monomer (m7), the units (m7) may be of one type, or of two or more types.

As other monomer other than the monomer (m7), for example, compounds listed as other monomers in the fluoropolymer (A1) may be mentioned.

Such other monomers other than the monomer (m7) may, for example, be N,N-dimethylaminoethyl (meth) acrylate, N,N-diethylaminoethyl (meth) acrylate, N-(meth)acryloyl morpholine, N-(meth)acryloyl pyridine, N,N-dimethylamino-oxide ethyl (meth)acrylate, N,N-diethylamino-oxide ethyl (meth)acrylate, etc. Further, 2-isocyanatoethyl (meth) acrylate, 3,5-dimethylpyrazole adduct of 2-isocyanatoethyl (meth)acrylate, 3-isocyanate propyl (meth)acrylate, 4-isocyanate butyl (meth)acrylate, triallyl isocyanurate, glycidyl (meth)acrylate, a polyoxyalkylene glycol monoglycidyl ether (meth)acrylate may also be used.

The proportion of units (m1) to all units in the fluoropolymer (A1) is preferably from 95 to 5 mol %, particularly preferably from 90 to 10 mol %. When the proportion of units (m1) is at least the above lower limit value, water resistance will be excellent. When the proportion of units (m1) is at most the above upper limit value, protein will be less likely to be adsorbed.

The proportion of units having a biocompatible group to all units in the fluoropolymer (A1) is preferably from 5 to 95 mol %, particularly preferably from 10 to 90 mol %. When the proportion of the units is at least the above lower limit value, protein will be less likely to be adsorbed. When the proportion of the units is at most the above upper limit value, water resistance will be excellent.

The total proportion of units (m2) and units (m3) to all units in the fluoropolymer (A1) is preferably from 5 to 95 mol %, particularly preferably from 10 to 90 mol %. When the total proportion of units (m2) and units (m3) is at least the above lower limit value, protein will be less likely to be adsorbed. When the total proportion of units (m2) and units (m3) is at most the above upper limit value, water resistance will be excellent.

In a case where the fluoropolymer (A1) has units (m7), the proportion of units (m7) to all units in the fluoropolymer (A1) is preferably from 0.1 to 10 mol %, particularly preferably from 0.5 to 10 mol %. When the proportion of units (m7) is at least the above lower limit value, water resistance will be excellent. When the proportion of units (m7) is at most the above upper limit value, protein will be less likely to be adsorbed.

The fluoropolymer (A1) is obtainable by carrying out a polymerization reaction of the monomers in a polymerization solvent by using a known method.

The polymerization solvent is not particularly limited, and may, for example, be a ketone (acetone, methyl ethyl ketone, methyl isobutyl ketone, etc.), an alcohol (methanol, 2-propyl alcohol, etc.), an ester (ethyl acetate, butyl acetate, etc.), an ether (diisopropyl ether, tetrahydrofuran, dioxane, etc.), a glycol ether (ethyl ether or methyl ether of ethylene glycol, propylene glycol or dipropylene glycol, etc.) and its derivatives, an aliphatic hydrocarbon, an aromatic hydrocarbon, a halogenated hydrocarbon (perchloroethylene, trichloro-1,1,1-ethane, trichlorotrifluoroethane, dichloropentafluoropropane, etc.), dimethylformamide, N-methyl-2-pyrrolidone, butyloacetone, dimethyl sulfoxide (DMSO), etc.

The total concentration of all monomers in the reaction solution in the polymerization reaction for obtaining the fluoropolymer (A1) is preferably from 5 to 60 mass %, particularly preferably from 10 to 40 mass %.

In the polymerization reaction for obtaining the fluorocopolymer (A1), it is preferred to use a polymerization initiator. The polymerization initiator may, for example, be a peroxide (benzyl peroxide, lauryl peroxide, succinyl peroxide, tert-butyl perpivalate, etc.), an azo compound, etc.

As the polymerization initiator, 2,2'-azobisisobutyronitrile, 2,2'-azobis-2-methylbutyronitrile, dimethyl-2,2'-azobis isobutyrate, 2,2'-azobis [2-(2-imidazolin-2-yl) propane], 2,2'-azobis(4-methoxy-2,4-dimethylvaleronitrile), 1,1'-azobis(2-cyclohexane-1-carbonitrile), 2,2'-azobis(2,4-dimethylvaleronitrile), 1,1'-azobis(1-acetoxy-1-phenylethane), dimethyl azobis isobutyrate, or 4,4'-azobis (4-cyanovaleric acid) is preferred, and 2,2'-azobisisobutyronitrile, 2,2'-azobis [2-(2-imidazolin-2-yl) propane] or 4,4'-azobis(4-cyanovaleric acid) is particularly preferred.

The amount of the polymerization initiator is preferably from 0.1 to 1.5 parts by mass, more preferably from 0.1 to 1.0 parts by mass, to the total amount of 100 parts by mass of monomers.

In order to adjust the polymerization degree (molecular weight) of the fluoropolymer (A1), a chain transfer agent may be used in the polymerization reaction. By using a chain transfer agent, there will also be an effect to increase the total concentration of monomers in the polymerization solvent.

The chain transfer agent may, for example, be an alkyl mercaptans (tert-dodecyl mercaptan, n-dodecyl mercaptan, stearyl mercaptan, etc.), aminoethanethiol, mercaptoethanol, 3-mercaptopropionic acid, 2-mercaptopropionic acid, thiomalic acid, thioglycolic acid, 3,3'-dithio-dipropionate, 2-ethylhexyl thioglycolate, n-butyl thioglycolate, methoxybutyl thioglycolate, ethyl thioglycolate, 2,4-diphenyl-4-methyl-1-pentene, carbon tetrachloride, etc.

The amount of the chain transfer agent is preferably from 0 to 2 parts by mass, more preferably from 0.1 to 1.5 parts by mass, to the total amount of 100 parts by mass of monomers.

The reaction temperature in the polymerization reaction is preferably within a range of from room temperature to the boiling point of the reaction solution. From the viewpoint of efficiently using the polymerization initiator, at least the half-life temperature of the polymerization initiator is preferred, from 30 to 90° C. is more preferred, and from 40 to 80° C. is further preferred.

«Fluoropolymer (A2)»

The fluoropolymer (A2) is a fluoropolymer having units (m1) derived from the following monomer (m1) and units (hereinafter referred to also as units (m4) derived from monomer (m4).

Monomer (m1): a monomer represented by the above formula (m1),

Monomer (m4): a monomer represented by the following formula (m4).

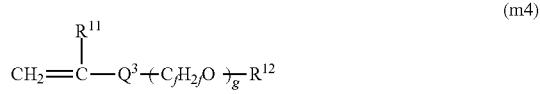

(m4)

Here, in the formula, $R^{11}$ is a hydrogen atom, a chlorine atom or a methyl group, $Q^3$ is —COO— or —COO(CH$_2$)$_h$—NHCOO— (wherein h is an integer of from 1 to 4), $R^{12}$ is a hydrogen atom or —(CH$_2$)$_i$—$R^{13}$ (wherein $R^{13}$ is a $C_{1-8}$ alkoxy group, a hydrogen atom, a fluorine atom, a trifluoromethyl group or a cyano group, and i is an integer of from 1 to 25), f is an integer of from 1 to 10, and g is an integer of from 1 to 100.

Monomer (m1):

The preferred range and exemplary of the monomer (m1) are the same as those described in the fluoropolymer (A1).

Units (m1) may be of one type, or of two or more types.

Monomer (m4):

The monomer (m4) is a monomer having a group (1).

In the formula (m4), $R^{11}$ is, from the viewpoint of polymerization efficiency, preferably a hydrogen atom or a methyl group, particularly preferably a methyl group.

$Q^3$ is preferably —COO—.

$R^{12}$ is preferably a hydrogen atom.

In a case where g is 2 or more, the plurality of (C$_f$H$_{2f}$O) may be the same or different. If different, their disposition may be any of random, block or alternating (e.g. (CH$_2$CH$_2$O—CH$_2$CH$_2$CH$_2$CH$_2$O), etc.). If f is 3 or more, C$_f$H$_{2f}$O may have a linear structure or a branched structure. (C$_f$H$_{2f}$O) may, for example, be (CH$_2$O), (CH$_2$CH$_2$O), (CH$_2$CH$_2$CH$_2$O), (CH(CH$_3$)CH$_2$O), (CH$_2$CH$_2$CH$_2$CH$_2$O), etc.

f is preferably an integer of from 1 to 6, particularly preferably an integer of from 1 to 4, from such a viewpoint that protein is less likely to be adsorbed.

g is preferably an integer of from 1 to 50, more preferably an integer of from 1 to 30, particularly preferably an integer of from 1 to 20, from such a viewpoint that an exclusion volume effect is high and protein is less likely to be adsorbed.

i is preferably an integer of from 1 to 4, particularly preferably 1 or 2, from the viewpoint of excellent flexibility of the fluoropolymer (A2).

$R^{13}$ is preferably an alkoxy group from such a viewpoint that protein is less likely to be adsorbed.

As the monomer (m4), a monomer (m41) represented by the following formula (m41) is preferred.

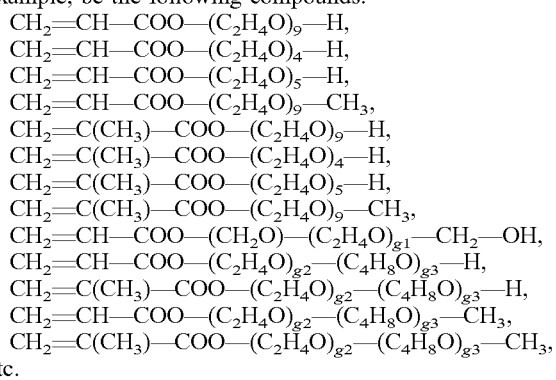
(m41)

Specific examples of the monomer (m4) may, for example, be the following compounds.

CH$_2$=CH—COO—(C$_2$H$_4$O)$_9$—H,
CH$_2$=CH—COO—(C$_2$H$_4$O)$_4$—H,
CH$_2$=CH—COO—(C$_2$H$_4$O)$_5$—H,
CH$_2$=CH—COO—(C$_2$H$_4$O)$_9$—CH$_3$,
CH$_2$=C(CH$_3$)—COO—(C$_2$H$_4$O)$_9$—H,
CH$_2$=C(CH$_3$)—COO—(C$_2$H$_4$O)$_4$—H,
CH$_2$=C(CH$_3$)—COO—(C$_2$H$_4$O)$_5$—H,
CH$_2$=C(CH$_3$)—COO—(C$_2$H$_4$O)$_9$—CH$_3$,
CH$_2$=CH—COO—(CH$_2$O)—(C$_2$H$_4$O)$_{g1}$—CH$_2$—OH,
CH$_2$=CH—COO—(C$_2$H$_4$O)$_{g2}$—(C$_4$H$_8$O)$_{g3}$—H,
CH$_2$=C(CH$_3$)—COO—(C$_2$H$_4$O)$_{g2}$—(C$_4$H$_8$O)$_{g3}$—H,
CH$_2$=CH—COO—(C$_2$H$_4$O)$_{g2}$—(C$_4$H$_8$O)$_{g3}$—CH$_3$,
CH$_2$=C(CH$_3$)—COO—(C$_2$H$_4$O)$_{g2}$—(C$_4$H$_8$O)$_{g3}$—CH$_3$,
etc.

In the above formulae, g1 is an integer of from 1 to 20, and g2 and g3 are each independently an integer of from 1 to 50.

As the monomer (m4), from such a viewpoint that protein is less likely to be adsorbed, the following compounds are preferred.

CH$_2$=CH—COO—(C$_2$H$_4$O)$_9$—H,
CH$_2$=CH—COO—(C$_2$H$_4$O)$_4$—H,
CH$_2$=CH—COO—(C$_2$H$_4$O)$_5$—H,
CH$_2$=C(CH$_3$)—COO—(C$_2$H$_4$O)$_9$—CH$_3$,
CH$_2$=CH—COO—(CH$_2$O)—(C$_2$H$_4$O)$_{g1}$—CH$_2$—OH,
CH$_2$=C(CH$_3$)—COO—(C$_2$H$_4$O)$_{g2}$—(C$_4$H$_8$O)$_{g3}$—H.

The fluoropolymer (A2) may have units derived from another monomer other than the monomer (m1) and the monomer (m4).

As such another monomer, from the viewpoint of excellent water resistance, a monomer (m5) represented by the following formula (m5) is preferred.

CH$_2$=CR$^{14}$—COO-Q$^4$-R$^{15}$     (m5)

Here, $R^{14}$ is a hydrogen atom, a chlorine atom or a methyl group, $R^{15}$ is a $C_{1-8}$ alkoxy group, a hydrogen atom, a hydroxy group or a cyano group, and $Q^4$ is a single bond, a $C_{1-20}$ alkylene group, a $C_{1-12}$ polyfluoroalkylene group or —CF$_2$—(OCF$_2$CF$_2$)$_y$—OCF$_2$— (wherein y is an integer of from 1 to 6).

In the formula (m5), $R^{14}$ is, from the viewpoint of polymerization efficiency, preferably a hydrogen atom or a methyl group, particularly preferably a hydrogen atom.

x is, from the viewpoint of excellent flexibility of the fluoropolymer (A2), preferably an integer of from 1 to 15, particularly preferably an integer of from 2 to 15.

The alkylene group and polyfluoroalkylene group for $Q^4$ may be linear or branched. $Q^4$ is, from the viewpoint of excellent flexibility of the fluoropolymer (A2), preferably a $C_{1-12}$ alkylene group, particularly preferably a methylene group or an isobutylene group.

$R^{15}$ is, from the viewpoint of excellent water resistance, preferably a hydrogen atom.

Specific examples of the monomer (m5) may, for example, be the following compounds.

CH$_2$=CH—COO—(CH$_2$)$_4$—H,
CH$_2$=CH—COO—(CH$_2$)$_6$—H,
CH$_2$=CH—COO—(CH$_2$)$_8$—H,
CH$_2$=CH—COO—(CH$_2$)$_{16}$—H,
CH$_2$=CH—COO—CH$_2$CH(C$_2$H$_5$)CH$_2$CH$_2$CH$_3$,
etc.

As the monomer (m5), CH$_2$=CH—COO—(CH$_2$)$_4$—H, CH$_2$=CH—COO(CH$_2$)$_8$—H or CH$_2$=CH—COO—(CH$_2$)$_{16}$—H is preferred, and CH$_2$=CH—COO—(CH$_2$)$_8$—H or CH$_2$=CH—COO—(CH$_2$)$_{16}$—H is particularly preferred.

From the viewpoint of excellent water resistance, it is also preferred that the fluoropolymer (A2) has units (m7) derived from a monomer (m7). The preferred embodiment of the monomer (m7) is the same as in the case of the fluoropolymer (A1).

Further, as another monomer other than the monomer (m5) and the monomer (m7), the same compound as the compound mentioned as another monomer other than the monomer (m7) in the fluoropolymer (A1) may be mentioned.

In a case where the fluoropolymer (A2) has units (m5), the units (m5) may be of one type, or of two or more types.

In a case where the fluoropolymer (A2) has units (m5) in addition to units (m1) and units (m4), particularly preferred is a fluoropolymer having CH$_2$=CHCOO(CH$_2$)$_2$(CF$_2$)$_5$CF$_3$ units, $CH_2=CH-COO-(CH_2O)-(C_2H_4O)_{g1}-CH_2-OH$ (g1=1 to 20) units, and $CH_2=CH-COO-(CH_2)_{16}-H$ units.

The proportion of units (m1) to all units in the fluoropolymer (A2) is preferably from 95 to 5 mol %, particularly preferably from 90 to 10 mol %. When the proportion of units (m1) is at least the above lower limit value, water resistance will be excellent. When the proportion of units (m1) is at most the above upper limit value, protein will be less likely to be adsorbed.

The proportion of units (m4) to all units in the fluoropolymer (A2) is preferably from 5 to 95 mol %, particularly preferably from 10 to 90 mol %. When the proportion of units (m4) is at least the above lower limit value, protein will be less likely to be adsorbed. When the proportion of units (m4) is at most the above upper limit value, water resistance will be excellent.

In a case where the fluoropolymer (A2) has units (m5), the proportion of units (m5) to the total of units (m1) and units (m4) is preferably from 5 to 95 mol %, particularly preferably from 10 to 90 mol %. When the proportion of units (m5) is at least the above lower limit value, water resistance will be excellent. When the proportion of units (m5) is at most the above upper limit value, protein will be less likely to be adsorbed.

In a case where the fluoropolymer (A2) has units (m7), the proportion of units (m7) to all units in the fluoropolymer (A2) is preferably from 0.1 to 10 mol %, particularly preferably from 0.5 to 10 mol %. When the proportion of units (m7) is at least the above lower limit value, water resistance will be excellent. When the proportion of units (m7) is at most the above upper limit value, protein will be less likely to be adsorbed.

In the case of using the monomers (m1), (m4), (m5) and (m7), the fluoropolymer (A2) may be produced in the same manner as the fluoropolymer (A1).

«Fluoropolymer (A3)»

The fluoropolymer (A3) is a block copolymer having a segment (I) comprising units (hereinafter referred to also as units (m6)) derived from a monomer (m6) represented by the following formula (m6) and a segment (II) comprising a molecular chain derived from a polymeric azo initiator having a structure (hereinafter referred to also as the structure (6)) represented by the following formula (6). The molecular chain of the structure (6) is made of a unit having a group (1) as a biocompatible group. Thus, the fluoropolymer (A3) has groups (1) in the main chain.

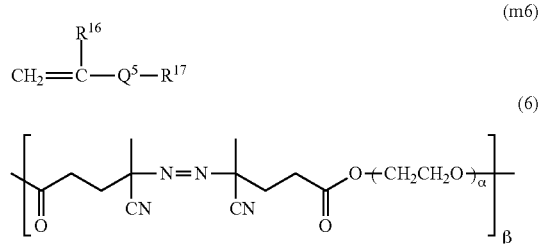

Here, in the above formulae, $R^{16}$ is a hydrogen atom, a chlorine atom and a methyl group, $Q^5$ is a single bond or a divalent organic group, $R^{17}$ is a $C_{1-6}$ polyfluoroalkyl group which may have an etheric oxygen atom between carbon-carbon atoms, α is an integer of from 5 to 300, and β is an integer of from 1 to 20.

Segment (I):

The segment (I) is a segment made of a molecular chain comprising units (m6).

In the formula (m6), $R^{16}$ is a hydrogen atom, a $C_{1-4}$ alkyl group or a halogen atom, and from the viewpoint of easy availability of raw material, a hydrogen atom or a methyl group is preferred.

$Q^5$ may, for example, be the following groups from the viewpoint of efficiency in synthesis and the physical properties of the fluoropolymer (A3).

—O—, —S—, —NH—, —SO$_2$—, —PO$_2$—, —CH=CH—, —CH=N—, —N=N—, —N(O)=N—, —COO—, —COO—, —COS—, —CONH—, —COCH$_2$—, —CH$_2$CH$_2$—, —CH$_2$—, —CH$_2$NH—, —CO—, —CH=CH—COO—, —CH=CH—CO—, a linear or branched alkylene group, an alkenylene group, an alkyleneoxy group, a divalent 4- to 7-membered ring substituent, a divalent 6-membered aromatic hydrocarbon group, a divalent 4- to 6-membered alicyclic hydrocarbon group, a divalent 5- or 6-membered heterocyclic group, a condensed ring thereof, a group constituted by a combination of divalent linking groups, etc.

A divalent organic group may have a substituent. The substituent may, for example, be a hydroxy group, a halogen atom (a fluorine atom, a chlorine atom, a bromine atom or an iodine atom), a cyano group, an alkoxy group (a methoxy group, an ethoxy group, a butoxy group, an octyloxy group, a methoxyethoxy group, etc.), an aryloxy group (a phenoxy group, etc.), an alkylthio group (a methylthio group, an ethylthio group, etc.), an acyl group (an acetyl group, a propionyl group, a benzoyl group, etc.), a sulfonyl group (a methanesulfonyl group, a benzene sulfonyl group), an acyloxy group (an acetoxy group, a benzoyloxy group), a sulfonyloxy group (a methanesulfonyloxy group, a toluene sulfonyloxy group, etc.), a phosphonyl group (a diethyl phosphonyl group, etc.), an amide group (an acetylamino group, a benzoylamino group, etc.), a carbamoyl group (an N,N-dimethylcarbamoyl group, N-phenylcarbamoyl group, etc.), an alkyl group (a methyl group, an ethyl group, a propyl group, an isopropyl group, a cyclopropyl group, a butyl group, a 2-carboxyethyl group, a benzyl group, etc.), an aryl group (a phenyl group, a tolyl group, etc.), a heterocyclic group (a pyridyl group, an imidazolyl group, a furanyl group, etc.), an alkenyl group (a vinyl group, a 1-propenyl group, etc.), an alkoxy acyloxy group (an acetyloxy group, a benzoyloxy group, etc.), an alkoxycarbonyl group (a methoxycarbonyl group, an ethoxycarbonyl group, etc.), a polymerizable group (a vinyl group, an acryloyl group, a methacryloyl group, a styryl group, a cinnamic acid residue, etc.), etc.

As $Q^5$, a single bond, —O—, —(CH$_2$CH$_2$O)$_\gamma$— (wherein γ is an integer of from 1 to 10), —COO—, a 6-membered aromatic hydrocarbon group, a linear or branched alkylene group, a linear or branched alkylene group in which part of hydrogen atoms has been substituted by a hydroxy group, or a group constituted by a combination of these bivalent linking groups, is preferred, and a single bond, a $C_{1-5}$ alkylene group or —COOY$^1$— is particularly preferred. Y$^1$ may, for example, be —(CH$_2$)$_\delta$—, —(CH$_2$)$_\delta$—CH(OH)—(CH$_2$)$_\epsilon$—, —(CH$_2$)$_\delta$—NR$^{18}$—SO$_2$—, etc., and —(CH$_2$)$_\delta$— is particularly preferred. Here, δ is an integer of from 1 to 5, ε is an integer of from 1 to 5, and $R^{18}$ is a hydrogen atom or a $C_{1-3}$ alkyl group.

In a case where $Q^5$ is —(CH$_2$CH$_2$O)$_\gamma$—, the fluoropolymer (A3) has a biocompatible group in both the main chain and side chain.

$R^{17}$ is a $C_{1-6}$ polyfluoroalkyl group which may have an etheric oxygen atom between carbon-carbon atoms. From the viewpoint of excellent water resistance, $R^{17}$ is preferably a $C_{3-6}$ polyfluoroalkyl group, particularly preferably a $C_4$ or $C_6$ polyfluoroalkyl group. $R^{17}$ may be linear or may be branched. Further, the polyfluoroalkyl group for $R^{17}$ is preferably a perfluoroalkyl group from the viewpoint of excellent water resistance.

Specific examples of the monomer (m6) may, for example, be the following compounds.

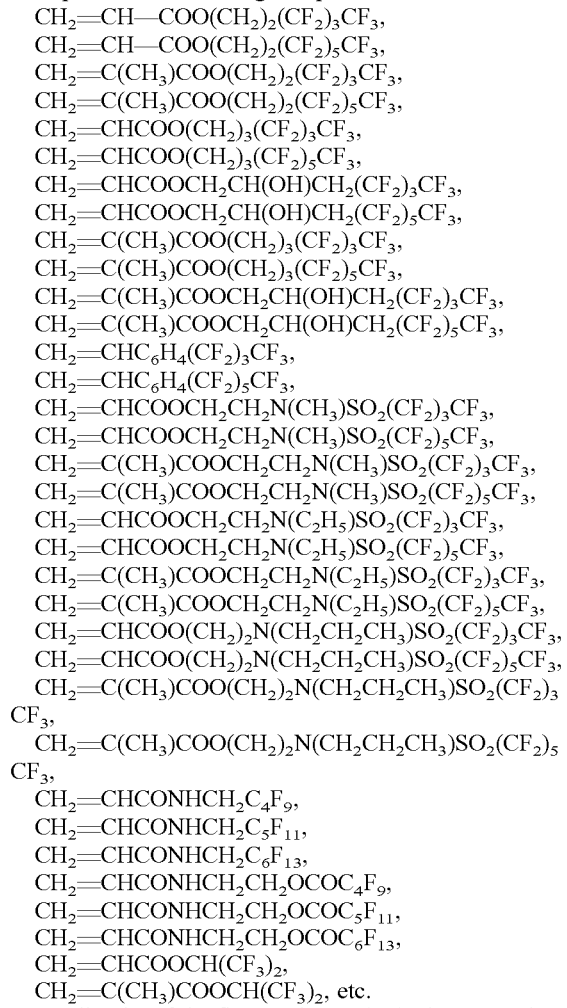

To all units of the fluoropolymer (A3), the proportion of units (m6) is preferably from 1 to 99 mol %, particularly preferably from 1 to 90 mol %. When the proportion of units (m6) is at least the above lower limit value, water resistance will be excellent. When the proportion of units (m6) is at most the above upper limit value, protein will be less likely to be adsorbed.

The proportion of units (m6) in the segment (I) (100 mass %) is preferably from 5 to 100 mass %, particularly preferably from 10 to 100 mass %. When the proportion of units (m6) is at least the lower limit value in the above range, polymerization of the monomers to constitute the segment (I) will be facilitated.

Segment (II):

The segment (II) is a segment made of a molecular chain derived from a polymeric azo initiator having the structure (6).

α in the formula (6) is an integer of from 5 to 300, and from such a viewpoint that protein is less likely to be adsorbed, it is preferably an integer of from 10 to 200, particularly preferably an integer of from 20 to 100.

β is an integer of from 1 to 20, and from the viewpoint of polymerization efficiency, it is preferably an integer of from 2 to 20, particularly preferably an integer of from 5 to 15.

The polymeric azo initiator having the structure (6) may, for example, be VPE series (VPE-0201, VPE-0401, VPE-0601) manufactured by Wako Pure Chemical Industries, Ltd., etc.

To all units in the fluoropolymer (A3), the total proportion of the respective units in the molecular chain of the structure (6) is preferably from 1 to 50 mol %, particularly preferably from 1 to 40 mol %. When the proportion of the units is at least the above lower limit value, protein will be less likely to be adsorbed. When the proportion is at most the above upper limit value, water resistance will be excellent.

The fluoropolymer (A3) can be produced by the same method as for the fluoropolymer (A1) except that the monomer (m6) and the polymeric azo initiator having the structure (6) are used. In the polymerization reaction for obtaining the fluoropolymer (A3), as a polymerization initiator, in addition to the polymeric azo initiator having the structure (6), the polymerization initiator mentioned in the case of the fluoropolymer (A1)) may be used in combination.

In the present invention, as the fluoropolymer (A), only one of the fluoropolymers (A1)) to (A3) may be used, or two or more selected from the group consisting of fluoropolymers (A1) to (A3) may be used in combination.

Further, the fluoropolymer (A) is not limited to the above-described fluoropolymers (A1)) to (A3).

[Coating Solution]
(Solvent)

The coating solution of the present invention contains a solvent (hereinafter referred to also as "solvent (B)") in addition to the fluoropolymer (A). When the protein adhesion inhibitor of the present invention is liquid at room temperature (from 20 to 25° C.), it may be applied as it is, but by applying the coating solution by wet coating, it is possible to easily form a coating layer formed from the protein adhesion inhibitor.

The coating solution of the present invention may be used, for example, for preventing adhesion of protein to a medical device. Specifically, by letting a medical device have a coating layer formed by using the coating solution of the present invention, it is possible to prevent adhesion of protein to the medical device.

At the time of applying the coating solution, components other than the fluoropolymer (A) and solvent (B), e.g. a leveling agent, a crosslinking agent, etc., may be incorporated in the coating solution for application. In a case where no crosslinking agent is incorporated in the coating solution, the coating layer will be a layer formed of only the fluoropolymer (A). Whereas, in a case where a crosslinking agent is incorporated in the coating solution, the coating layer will be a layer formed from the fluoropolymer (A) and the crosslinking agent.

The solvent (B) may, for example, be a non-fluorinated solvent, a fluorinated solvent, etc., and the non-fluorinated solvent may, for example, be an alcohol solvent, a halogen-containing solvent, etc. For example, ethanol, methanol, acetone, chloroform, ASAHIKLIN AK225 (manufactured by Asahi Glass Company, Limited), AC6000 (manufactured by Asahi Glass Company, Limited), etc. may be mentioned. As the solvent (B), it is preferred to select the type that does not dissolve the device, etc. In the case of using polystyrene as the material for the device, ethanol, methanol, ASAHIK-LIN AK225 (manufactured by Asahi Glass Company, Limited), AC6000 (manufactured by Asahi Glass Company, Limited), etc. are preferred.

The concentration of the fluoropolymer (A) in the coating solution of the present invention is preferably from 0.0001 to 10 mass %, particularly preferably from 0.0005 to 5 mass %. When the concentration of the fluoropolymer (A) is within the above range, it is possible to uniformly apply the coating solution thereby to form a uniform coating layer.

(Other Components)

The coating solution of the present invention may contain other components other than the fluoropolymer (A) and solvent (B), as the case requires.

Other components may, for example, be a leveling agent, a crosslinking agent, etc.

In a case where a device is to be used for a long time, by adding to the coating solution a crosslinking agent capable of crosslinking the fluoropolymer (A) thereby to adjust the degree of crosslinking in the coating layer, it is possible to form a coating layer having excellent durability whereby excellent biocompatibility can be maintained over a longer period of time. Specifically, when the fluoropolymer (A) has a hydroxy group, by adding a cross-linking agent which reacts with the hydroxy group, it is possible to form a coating layer having excellent durability. Particularly in the case of using a fluoropolymer comprising units having a hydroxy group (e.g. a fluoropolymer (A2) comprising units (m4) wherein $R^{12}$ is a hydrogen atom), it is preferred to add a crosslinking agent that reacts with the hydroxy group.

As the crosslinking agent which reacts with a hydroxy group, a polyfunctional isocyanate compound may be mentioned. The polyfunctional isocyanate compound may, for example, be hexamethylene diisocyanate (HDI), a HDI-type polyisocyanate, isophorone diisocyanate (IPDI), etc. The HDI-type polyisocyanate may, for example, be a biuret type for the two-liquid type, an isocyanurate type, an adduct type, a bifunctional type, etc., and also includes a block type having a threshold value in the curing initiation temperature. As the HDI-type polyisocyanate, a commercially available product may be used, and Duranate (manufactured by Asahi Kasei Corporation), etc. may be mentioned.

The polyfunctional isocyanate compound to be used, may be suitably selected for use depending upon the reaction temperature, the material for the device. For example, in a case where polystyrene is used as the material for the device, a biuret type, an isocyanurate type or the like is preferred, which can be dissolved in ASAHIKLIN AK225 (manufactured by Asahi Glass Company, Limited), AC6000 Asahi Glass Company, Limited), etc., and whereby a curing reaction proceeds even at a temperature of not higher than 80° C. as the heat distortion temperature of polystyrene.

The degree of crosslinking in the coating layer is determined by the amount of hydroxy groups in the fluoropolymer (A), the amount of the crosslinking agent to be added and the reaction rate, and may be suitably adjusted within a range not to impair the effects of the present invention.

The amount of the crosslinking agent is preferably from 0.01 to 10 parts by mass, particularly preferably from 0.1 to 1 part by mass, per 100 parts by mass of the fluoropolymer (A). When the amount of the crosslinking agent is at least the lower limit value in the above range, it is easy to form a coating layer excellent in durability.

When the amount of the crosslinking agent is at most the upper limit value in the above range, it is easy to form a coating layer excellent in the biocompatibility.

As described above, the protein adhesion inhibitor and the coating solution of the present invention contain the fluoropolymer (A) having biocompatible groups and having the proportion P controlled to be within a specific range, whereby it is possible to easily form a coating layer which is excellent in water resistance, from which coating components are less likely to be eluted, on which protein is less likely to be adsorbed, and which is excellent in biocompatibility.

As an application of the protein adhesion inhibitor and the coating solution of the present invention, a medical device is particularly effective.

Further, the protein adhesion inhibitor and the coating solution of the present invention may also be used for marine structures such as ships, bridges, marine tanks, port facilities, submarine bases, offshore oil drilling equipment, etc. By applying the protein adhesion inhibitor of the present invention to a marine structure, it is possible to prevent adhesion of protein to the marine structure. As a result, it is possible to prevent adhesion of aquatic organisms such as shellfish (barnacles, etc.), seaweeds (green laver, sea lettuce, etc.), etc.

[Medical Device]

The medical device of the present invention comprises a device substrate and a coating layer formed from the protein adhesion inhibitor of the present invention, on the device substrate.

Specific examples of the medical device may, for example, be pharmaceuticals, quasi-drugs, medical tools, etc. The medical tools are not particularly limited and may, for example, be cell culture vessels, cell culture sheets, vials, plastic-coated vials, syringes, plastic-coated syringes, ampoules, plastic coated ampoules, cartridges, bottles, plastic-coated bottles, pouches, pumps, sprayers, plugs, plungers, caps, lids, needles, stents, catheters, implants, contact lenses, micro-channel chips, drug delivery system materials, artificial blood vessels, artificial organs, blood dialysis membranes, guard wires, blood filters, blood storage packs, endoscopes, bio-chips, sugar chain synthesis equipment, molding auxiliary materials, packaging materials, etc. Among them, cell culture vessels are preferred.

Figure 2:
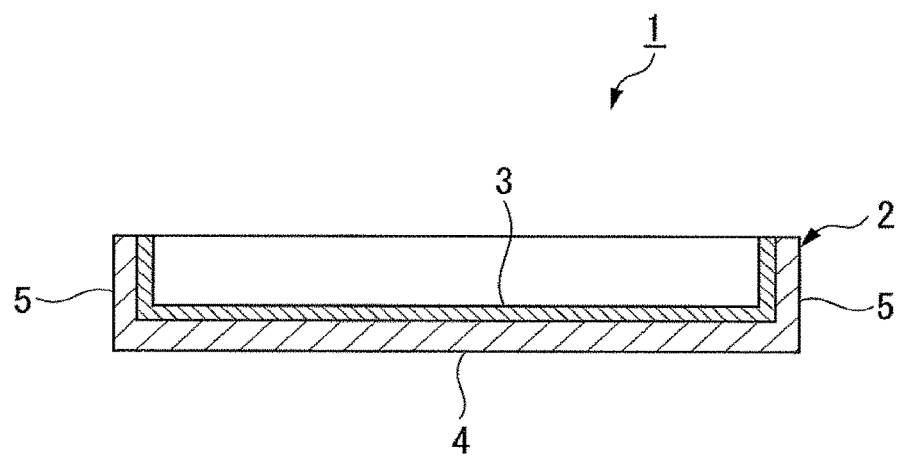
FIG. 2 is a I-I cross-sectional view of the medical device in FIG. 1.

As a specific example of the medical device of the present invention, a medical device 1 illustrated in FIGS. 1 and 2 may, for example, be mentioned. The medical device 1 is a petri dish which is one of cell culture vessels.

The medical device 1 comprises a device substrate 2 and a coating layer 3 formed on the device substrate 2. The device substrate 2 comprises a bottom portion 4 having a circular shape in plan view, and a side surface portion 5 which rises along the entire circumference of the peripheral edge of the bottom surface portion 4, and has a shape of a container with the top being open. The coating layer 3 is formed on the inner surface of the device substrate 2, i.e. on the upper side of the bottom portion 4 and the inner side of the side surface portion 5, by the protein adhesion inhibitor of the present invention.

The material for forming the device substrate in the medical device of the present invention is not particularly limited, and may, for example, be a resin, such as polystyrene, polycarbonate, polypropylene, etc., glass, etc. Among them, the present invention is particularly effective in a case where the material for forming the device substrate is glass.

The coating layer may, for example, be a layer formed solely of the fluoropolymer (A), or a layer formed from the fluoropolymer (A) and a crosslinking agent.

The thickness of the coating layer is preferably from 1 nm to 1 mm, particularly preferably from 5 nm to 800 μm. When the thickness of the coating layer is at least the above lower limit value, protein will be less likely to be adsorbed. When the thickness of the coating layer is at most the above upper limit value, the coating layer tends to intimately adhere to the surface of the device substrate.

In order to improve the adhesion between the coating layer and the device substrate, an adhesive layer may be provided between the coating layer and the device substrate. As the adhesive for forming the adhesive layer, one which exhibits sufficient adhesion to both the coating layer and the device substrate, may suitably be used, and for example, a cyanoacrylate adhesive as an adhesive for a fluororesin, a silicone modified acrylic adhesive, an epoxy-modified silicone adhesive, etc. may be mentioned.

As a specific example, in the case of using polystyrene as the material for forming the device substrate, a cyanoacrylate adhesive may be used. In this case, at the device substrate side of the adhesive layer, a cyanoacrylate monomer in the cyanoacrylate adhesive will be reacted with and cured by moisture in the air or at the surface of the device substrate. In the coating layer, biocompatible groups derived from the fluoropolymer (A) are present, and therefore, moisture is present in the coating layer and in its vicinity. Therefore, also on the coating layer side of the adhesive layer, a cyanoacrylate monomer will be reacted with and cured by such moisture. By the adhesive layer, it is possible to improve the adhesion between the coating layer and the device substrate.

(Method for Producing Medical Device)

As a method for producing a medical device of the present invention, for example, the following method comprising a coating step and a drying step may be mentioned.

Coating step: a step of applying the coating solution of the present invention on a device substrate.

Drying step: a step of removing the solvent derived from the coating solution to obtain a medical device having a coating layer formed on the device substrate.

<Coating Step>

As a method of applying the coating solution, a known method may be employed, and, for example, a method may be mentioned which is conducted by using a coating device such as a brush, a roller, a dipping device, a spray, a roll coater, a die coater, an applicator, a spin coater, etc.

<Drying Step>

The method of removing the solvent derived from the coating solution applied on the device substrate is not particularly limited, and, for example, it is possible to use a known drying method such as air drying or drying by heating.

The drying temperature is preferably from 30 to 200° C., more preferably from 30 to 150° C.

The method for producing a medical device of the present invention is not limited to the above-described method, and in a case where the protein adhesion inhibitor of the present invention is liquid at room temperature (from 20 to 25° C.), the protein adhesion inhibitor may be applied as it is, to form a coating layer. In this case, in order to improve the adhesion to the surface of the device substrate, the protein adhesion inhibitor may be heated.

As described above, the medical device of the present invention has a coating layer formed from the protein adhesion inhibitor of the present invention on the device surface, whereby water resistance is excellent, coating components are less likely to be eluted, protein is less likely to be adsorbed, and biocompatibility is excellent.

EXAMPLES

Now, the present invention will be described in detail with reference to Examples, but the present invention is not limited by the following description. Ex. 1 to 3, 6, 7, 9 to 14, 16 to 21, and 23 to 30, are Examples of the present invention, and Ex. 4, 5, 8, 15, and 22, are Comparative Examples.

[Copolymer Composition]

20 mg of a fluoropolymer obtained, was dissolved in chloroform, and the copolymer composition was determined by $^1$H-NMR.

[Fluorine Atom Content]

The fluorine atom content was determined by $^1$H-NMR, ion chromatography and elemental analysis.

[Glass Transition Temperature (Tg)]

The glass transition temperature of a fluoropolymer was measured by raising or lowering the temperature between −30° C. to 200° C. at a rate of 10° C./min. by DSC (manufactured by TA Instruments). The temperature for a change from the rubber state to the glass state in the second cycle of the temperature lowering, was adopted as the glass transition temperature.

[Molecular Weight]

The number average molecular weight (Mn), mass average molecular weight (Mw) and molecular weight distribution (mass average molecular weight (Mw)/number average molecular weight (Mn)) of a fluoropolymer, were measured by means of a GPC device (HLC8220, manufactured by Tosoh Corporation) using tetrahydrofuran (THF) as a solvent.

[Proportion P] The proportion P was calculated by the following formula. The proportion (mass %) of units having a biocompatible group to all units in a fluoropolymer, was measured by $^1$H-NMR (JEOL, Inc. AL300), ion chromatography (Dionex DX500) and elemental analysis (Perkin Elmer 2400-CHSN).

(Proportion $P$)=[(proportion (mass %) of units having a biocompatible group to all units in a fluoropolymer)/(fluorine atom content (mass %))]×100

[Evaluation Methods]

(Water-insolubility)

10 mg of a fluoropolymer used in each Ex. and 1 g of water were weighed into a sample tube and stirred for 1 hour at room temperature, whereupon the water-insolubility was visually confirmed. The evaluation was carried out on the basis of the following standards.

<Evaluation Standards>

○ (good): The fluoropolymer remained.

x (bad): The fluoropolymer was completely dissolved and did not remain.

(Protein Non-adsorption)

<Protein Non-adsorption Test>

(1) Preparation of Coloring Solution and Protein Solution

As the coloring solution, one having 50 mL of a peroxidase color solution (3,3',5,5'-tetramethylbenzidine (TMBZ), manufactured by KPL, Inc.) and 50 mL of TMB Peroxidase Substrate (manufactured by KPL, Inc.) mixed, was used.

As the protein solution, one having protein (POD-goat anti mouse IgG, manufactured by Bio-Rad Laboratories, Inc.) diluted to 16,000-fold with phosphate buffered saline (D-PBS, manufactured by Sigma Co.), was used.

(2) Protein Adsorption

To 3 wells of a 24-well microplate having a coating layer formed on each well surface, 2 mL of the protein solution was dispensed (using 2 mL per well) and left to stand at room temperature for one hour.

As a blank, the protein solution was dispensed to 3 wells of a 96-well microplate in an amount of 2 μL (using 2 μL per well).

(3) Washing of Wells

Then, the 24-well microplate was washed four times with 4 mL of phosphate buffered saline (D-PBS, manufactured by Sigma Co.) having 0.05 mass % of a surfactant (Tween 20, manufactured by Wako Pure Chemical Industries, Ltd.) incorporated (using 4 mL per well).

(4) Dispensing of Coloring Solution

Then, to the washed 24-well microplate, 2 mL of the coloring solution was dispensed (using 2 mL per well), and a coloring reaction was carried out for 7 minutes. The coloring reaction was stopped by adding 1 mL of 2N sulfuric acid (using 1 mL per well).

As the blank, to the 96-well microplate, 100 µL of the coloring solution was dispensed (using 100 µL per well), and a coloring reaction was carried out for 7 minutes. The coloring reaction was stopped by adding 50 µL of 2N sulfuric acid (using 50 µL per well).

(5) Preparation for Measurement of Absorbance

Then, from each well of the 24-well microplate, 150 µL of the liquid was taken and transferred to the 96-well microplate.

(6) Measurement of Absorbance and Protein Adsorption Rate Q

As to the absorbance, the absorbance at 450 nm was measured by MTP-810Lab (manufactured by Corona Electric Co., Ltd.). Here, the average value of the absorbance (N=3) of the blank was designated as $A_0$. The absorbance of the liquid transferred from the 24-well microplate to the 96-well microplates was designated as $A_1$.

The protein adsorption rate $Q_1$ was obtained by the following formula, and the protein adsorption rate Q was set to be the average value.

$$Q_1 = A_1/\{A_0 \times (100/\text{dispensed amount of the protein solution in the blank})\} \times 100 = A_1/\{A_0 \times (100/2\ \mu L)\} \times 100 [\%]$$

(Cell Non-adhesion)

<Cell Culture Test Using TIG-3 Cells>

Using 10% FBS/MEM (MEM Life-Technologies, Inc., Code #11095-098), a cell suspension of $1.5 \times 10^4$ cells/mL, of TIG-3 cells (Human Science Foundation Research Resources Bank, Cell Number: JCRB0506), was prepared.

To a polystyrene microplate (number of wells: 24) having a coating layer formed on each well surface, the above cell suspension was added in an amount of 1 mL/well. After 4 days of culturing, the presence or absence of cell adhesion was confirmed by using a microscope. Further, an Alamar Blue solution (manufactured by Invitrogen, trade name alamarBlue Code DAL1100) in an amount of 1/10 volume of the culture medium was added to the culture solution, followed by culturing for 4 hours. Thereafter, fluorescence measurement was conducted at an excitation wavelength of 530 nm and at a detection wavelength of 590 nm, and the physiological activity of cells remaining as adhered, was quantitated. Further, after washing away the non-adherent cells with phosphate buffered saline (D-PBS, manufactured by Sigma Co.), methanol fixation was conducted so that only cells remaining as adhered, were stained with Giemsa stain (manufactured by Kanto Chemical Co., Inc., Code #17596-23).

Evaluation of cell non-adhesion was carried out by the following standards.

Evaluation Standards:

○ (good): By observation by means of a phase contrast microscope, cells were not bonded and progressed, and adherent cells were not confirmed also by Giemsa staining.

x (bad): By observation by means of a phase contrast microscope, cells were adhered and progressed, or adherent cells were confirmed by Giemsa staining.

<Cell Culture Test Using HepG2 Cells (Long-term Culturing)

Using 10% FBS/DMEM (DMEM Life-Technologies Inc., trade name Code #11885-092), a cell suspension of $5 \times 10^3$ cells/mL, of HepG2 cells (Human Science Foundation Research Resources Bank, Cell Number: JCRB1054), was prepared.

To a polystyrene microplate having a coating layer formed on each well surface, the above cell suspension was added in an amount of 1 mL/well. After 14 days of culturing, the presence or absence of cell adhesion was confirmed by using a microscope. Further, non-adherent cells were washed away with phosphate-buffered saline (D-PBS, manufactured by Sigma Co.), and only cells remaining as adhered were stained with Giemsa stain (manufactured by Kanto Chemical Co., Inc., Code #17596-23).

Evaluation of cell non-adhesion was carried out by the following standards.

Evaluation Standards:

○ (good): By observation by means of a phase contrast microscope, cells were not bonded and progressed, and adherent cells were not confirmed also by Giemsa staining.

x (bad): By observation by means of a phase contrast microscope, cells were adhered and progressed, or adherent cells were confirmed by Giemsa staining.

(Durability of Coating Layer)

(1) Durability of Coating Layer Formed on the Well Surface of Microplate

In each Ex. given below, a 24-well microplate having a coating layer formed on the well surface, was immersed in water of 37° C. for one week, and then heated and dried at 60° C. for 2 hours. Thereafter, the above-described protein non-adsorption test was conducted to measure the protein adsorption rate Q, and the durability of the coating layer was evaluated according to the following standards. Here, the rate of increase in protein adsorption rate Q was calculated by the following formula.

Rate of increase in protein adsorption rate $Q$ (%)= (protein adsorption rate (%) after immersion in water of 37° C. for one week÷initial protein adsorption rate (%)−1)×100

Evaluation Standards:

○ (good): As compared to initial, the rate of increase in protein adsorption rate Q after the immersion is less than 5%.

Δ (acceptable): As compared to initial, the rate of increase in protein adsorption rate Q after the immersion is at least 5% and less than 20%.

x (bad): As compared to initial, the rate of increase in protein adsorption rate Q after immersion is at least 20%.

(2) Durability of Coated Layer Formed on the Surface of Glass Petri Dish

In each Ex. given below, 6 mL of water was put in a glass petri dish having a coating layer formed on the surface and left to stand for 24 hours in an oven at 40° C. Then, after removing the water, the glass petri dish was heated and dried at 100° C. for 1 hour in an oven. Thereafter, the above-described protein non-adsorption test was conducted to measure the protein adsorption rate Q, and the durability of the coating layer was evaluated according to the following standards. Here, the substrate adhesion ratio Z was calculated by the following formula.

Substrate adhesion rate Z=protein adsorption rate (%) after being left to stand at 40° C. for 24 hours with water put therein initial protein adsorption rate (%)

As the value of the substrate adhesion rate is small, the durability of the coating layer is excellent.

[Raw Materials]

The abbreviations of the raw materials used in the preparation of the fluoropolymers are shown below.

(Monomers)

C6FMA: $CH_2\!=\!C(CH_3)COO(CH_2)_2(CF_2)_5CF_3$.
C6FA: $CH_2\!=\!CHCOO(CH_2)_2(CF_2)_5CF_3$.
C1FMA: $CH_2\!=\!C(CH_3)COOCH_2CF_3$.
CBA: N-acryloyloxyethyl-N,N-dimethyl ammonium-α-N-methyl carboxybetaine.
CBMA: N-methacryloyloxyethyl-N,N-dimethyl ammonium-α-N-methyl carboxybetaine.
MPC: 2-methacryloyloxyethyl phosphorylcholine.
2-EHA: 2-ethylhexyl acrylate ($CH_2\!=\!CHCOOCH_2CH(C_2H_5)CH_2CH_2CH_3$).
PEG9A: polyethylene glycol monoacrylate (EO number average 9) ($CH_2\!=\!CHCOO(C_2H_4O)_9H$).
OMA: octyl methacrylate ($CH_2\!=\!C(CH_3)COO(CH_2)_8H$).
PEG4.5A: polyethylene glycol mono acrylate (EO number average 4.5) ($CH_2\!=\!CHCOO(C_2H_4O)_{4.5}H$).
PEPEGA: $CH_2\!=\!CHCOO(C_2H_4O)_{10}(C_3H_6O)_{20}(C_2H_4O)_{10}H$.
MPEG9MA: $CH_2\!=\!C(CH_3)COO(C_2H_4O)_9CH_3$.
PEBMA: $CH_2\!=\!C(CH_3)COO[(C_2H_4O)_{10}(C_4H_8O)_5]H$.
DAEMA: N,N-dimethylaminoethyl methacrylate.
IMADP: 3,5-dimethylpyrazole adduct of 2-isocyanatoethyl methacrylate (compound represented by the following formula (7)).
KBM-503: 3-methacryloyloxypropyl trimethoxysilane (product name "KBM-503", manufactured by Shin-Etsu Silicone Co., Ltd.).

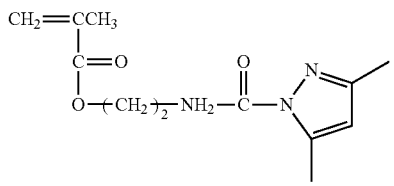

(7)

(Polymerization Initiators)

AIBN: 2,2'-azobisisobutyronitrile.
VPE: trade name "VPE-0201" (polymeric azo initiator having the structure (6), manufactured by Wako Pure Chemical Industries, Ltd.).

(Polymerization Solvent)

EtOH: ethanol.
MP: 1-methoxy-2-propanol.

Production Example 1

0.886 g (3.0 mmol) of MPC and 3.025 g (7.0 mmol) of C6FMA were weighed into a 300 mL three-necked flask, and 0.391 g of AIBN as a polymerization initiator, and 15.6 g of ethanol (EtOH) as a polymerization solvent were added. The molar ratio of C6FMA to MPC was made to be C6FMA/MPC=70/30, the total concentration of the monomers in the reaction solution was made to be 20 mass %, and the initiator concentration was made to be 1 mass %.

Inside of the flask was thoroughly purged with argon, then sealed and heated for 16 hours at 75° C. to conduct a polymerization reaction. The reaction mixture was cooled with ice and then, dropped in diethyl ether, to precipitate the polymer. The obtained polymer was sufficiently washed with diethyl ether, and then dried under reduced pressure to obtain a white powdery fluoropolymer (A-1).

The copolymer composition of the obtained fluoropolymer (A-1) was measured by H-NMR, and found to be C6FMA units/MPC units=44/56 (molar ratio).

Production Examples 2 to 15

Each polymer was obtained in the same manner as in Production Example 1 except that the types and charged amounts of monomers, and the type of the polymerization solvent were changed as shown in Table 1.

The charged ratio of monomers, the amount of the polymerization initiator added, and the type of the polymerization solvent, as well as the type, copolymer composition and fluorine atom content in the obtained fluoropolymer in each of Production Examples 1 to 15, are shown in Table 1.

TABLE 1

| Production Example | Charged ratio of monomers | | Polymerization initiator [mass %] | Polymerization solvent | Fluoropolymer | | | | | |
|---|---|---|---|---|---|---|---|---|---|---|
| | Molar ratio | Mass ratio | | | Type | Copolymer composition | | Fluorination content [mass %] | Tg [° C.] |
| | | | | | | Molar ratio | Mass ratio | | |
| 1 | C6FMA/MPC 70/30 | C6FMA/MPC 77/23 | AIBN1 | EtOH | A-1 | C6FMA/MPC 44/56 | C6FMA/MPC 54/46 | 30.6 | 117 |
| 2 | C6FMA/MPC 50/50 | C6FMA/MPC 59/41 | AIBN1 | EtOH | A-2 | C6FMA/MPC 41/59 | C6FMA/MPC 50/50 | 28.8 | 147 |
| 3 | C6FMA/MPC 30/70 | C6FMA/MPC 39/61 | AIBN1 | EtOH | A-3 | C6FMA/MPC 21/79 | C6FMA/MPC 28/72 | 16.0 | 172 |
| 4 | C6FMA/MPC 20/80 | C6FMA/MPC 27/73 | AIBN1 | EtOH | X-1 | C6FMA/MPC 14/86 | C6FMA/MPC 19/81 | 11.0 | 178 |
| 5 | C1FMA 100 | C1FMA 100 | AIBN1 | MP | X-2 | C1FMA 100 | C1FMA 100 | 33.9 | 196 |

TABLE 1-continued

| Production | Charged ratio of monomers | | Polymerization initiator | Polymerization solvent | Fluoropolymer | | | Fluorination content | Tg |
| --- | --- | --- | --- | --- | --- | --- | --- | --- | --- |
| | | | | | | Copolymer composition | | | |
| Example | Molar ratio | Mass ratio | [mass %] | | Type | Molar ratio | Mass ratio | [mass %] | [° C.] |
| 6 | C1FMA/MPC 70/30 | C1FMA/MPC 57/43 | AIBN1 | EtOH | A-4 | C1FMA/MPC 66/34 | C1FMA/MPC 53/47 | 17.8 | 132 |
| 7 | C1FMA/MPC 60/40 | C1FMA/MPC 46/54 | AIBN1 | EtOH | A-5 | C1FMA/MPC 54/46 | C1FMA/MPC 40/60 | 13.6 13.6 | 147 147 |
| 8 | C1FMA/MPC 50/50 | C1FMA/MPC 36/64 | AIBN1 | EtOH | X-3 | C1FMA/MPC 44/56 | C1FMA/MPC 32/68 | 10.5 | 168 |
| 9 | C6FMA/CBMA 50/50 | C6FMA/CBMA 67/33 | AIBN1 | EtOH | A-6 | C6FMA/CBMA 52/48 | C6FMA/CBMA 69/31 | 39.2 | 121 |
| 10 | C6FMA/CBMA 30/70 | C6FMA/CBMA 46/54 | AIBN1 | EtOH | A-7 | C6FMA/CBMA 30/70 | C6FMA/CBMA 46/54 | 26.5 | 155 |
| 11 | C6FMA/CBMA 20/80 | C6FMA/CBMA 33/67 | AIBN1 | EtOH | A-8 | C6FMA/CBMA 20/80 | C6FMA/CBMA 33/67 | 19.1 | 173 |
| 12 | C6FMA/CBA 50/50 | C6FMA/CBA 59/41 | AIBN1 | EtOH | A-9 | C6FMA/CBA 50/50 | C6FMA/CBA 59/41 | 33.7 | |
| 13 | C6FMA/CBA 30/70 | C6FMA/CBA 48/52 | AIBN1 | EtOH | A-10 | C6FMA/CBA 30/70 | C6FMA/CBA 48/52 | 27.4 | |
| 14 | C6FMA/CBA 20/80 | C6FMA/CBA 35/65 | AIBN1 | EtOH | A-11 | C6FMA/CBA 20/80 | C6FMA/CBA 35/65 | 20.0 | |
| 15 | CBA 100 | CBA 100 | AIBN1 | EtOH | X-4 | CBA 100 | CBA 100 | 0 | |

Production Example 16

5 g (11.6 mmol) of C6FMA was weighed into a 300 mL three-necked flask, and 0.7 g of VPE as a polymerization initiator and 13.3 g of MP as a polymerization solvent were added. The total concentration of monomers in the reaction mixture was made to be 30 mass %, and the charged molar ratio of C6FMA to VPE was made to be C6FMA/VPE=97/3.

Inside of the flask was thoroughly purged with argon, and then, sealed and heated for 16 hours at 75° C. to conduct a polymerization reaction. The reaction solution was cooled with ice and then dropwise added to diethyl ether to precipitate the polymer.

The obtained polymer was sufficiently washed with diethyl ether and then dried under reduced pressure to obtain a white powdery fluoropolymer (A-12).

Production Examples 17 to 19

Each polymer was obtained in the same manner as in Production Example 16 except that the types of monomers, and the charged ratio of monomers to a polymerization initiator, were changed as shown in Table 2.

The types and charged ratios of monomers and polymerization initiator, the type of the polymerization solvent, as well as the type, copolymer composition and fluorine atom content of the obtained fluoropolymer in each of Production Examples 16 to 19, are shown in Table 2. Here, "NA" in Table 2 means that the glass transition temperature was not detected.

TABLE 2

| Production | Charged ratio (Polymerization initiator/monomer) | | Polymerization solvent | Fluoropolymer | | | Fluorination content | Tg |
| --- | --- | --- | --- | --- | --- | --- | --- | --- |
| | | | | | Copolymer composition | | | |
| Example | Molar ratio | Mass ratio | | Type | Molar ratio | Mass ratio | [mass %] | [° C.] |
| 16 | C6FMA/VPE 97/3 | C6FMA/VPE 88/12 | MP | A-12 | C6FMA/VPE 97/3 | C6FMA/VPE 88/12 | 50.3 | NA |
| 17 | C6FMA/VPE 94/6 | C6FMA/VPE 78/22 | MP | A-13 | C6FMA/VPE 94/6 | C6FMA/VPE 78/22 | 44.6 | NA |
| 18 | C6FMA/VPE 92/8 | C6FMA/VPE 70/30 | MP | A-14 | C6FMA/VPE 92/8 | C6FMA/VPE 70/30 | 40 | NA |
| 19 | C1FMA/VPE 97/3 | C1FMA/VPE 70/30 | MP | A-15 | C1FMA/VPE 97/3 | C1FMA/VPE 70/30 | 23.8 | NA |

Production Example 20

In a 100 mL pressure-resistant glass bottle, 40 g of 2-EHA, 40 g of PEG9A, 0.66 g of V-601 (oil-soluble azo polymerization initiator, manufactured by Wako Pure Chemical Industries, Ltd.) and 49.8 g of m-xylene hexafluoride (manufactured by Central Glass Co., Ltd., hereinafter referred to as "m-XHF") were charged, and then, sealed and heated for 16 hours at 70° C. To this reaction solution, 20 g of C6FA, 40 g of m-XHF and 0.48 g of V-601 were charged, and then, sealed and heated for 16 hours at 70° C., to obtain a fluoropolymer (A-16). The copolymer composition of the fluoropolymer (A-16) was measured. As a result, it was found to be a fluoropolymer having PEG9A units, C6FA units and 2-EHA units in a molar ratio of 24:14:62 (mass ratio of 40:20:40). As a result of measurement of the molecular weight, the number average molecular weight (Mn) of the fluoropolymer (A-16) was 17,000, the mass average molecular weight (Mw) was 40,000, and the molecular weight distribution (mass average molecular weight (Mw)/number average molecular weight (Mn)) was 2.3.

Production Example 21

In a 100 mL pressure-resistant glass bottle, 15 g of OMA, 35 g of PEG4.5A, 0.41 g of V-601 and 31.3 g of m-XHF, were charged, and then, sealed and heated for 16 hours at 70° C. To this reaction solution, 50 g of C6FMA, 100 g of m-XHF and 1.2 g of V-601, were charged, and then sealed and heated for 16 hours at 70° C., to obtain a fluoropolymer (A-17).

The copolymer composition of the fluoropolymer (A-17) was measured. As a result, it was confirmed to be a fluoropolymer having PEG4.5A units, C6FMA units and OMA units in a molar ratio of 40:36:24 (mass ratio of 35:50:15).

Production Example 22

In a 100 mL pressure-resistant glass bottle, 80 g of PEPEGA, 0.66 g of V-601 and 49.8 g of m-XHF, were charged, and then, sealed and heated for 16 hours at 70° C. To this reaction solution, 20 g of C6FA, 40 g of m-XHF and 0.48 g of V-601, were charged, and then, sealed and heated for 16 hours at 70° C., to obtain a fluoropolymer (A-18). The copolymer composition of the fluoropolymer (A-18) was measured. As a result, it was confirmed to be a fluoropolymer having PEPEGA units and C6FA units in a molar ratio of 44:56 (mass ratio of 80:20).

Production Example 23

10.8 g (54 parts by mass) of C6FMA, 5.2 g (26 parts by mass) of MPEG9MA, 3.2 g (16 parts by mass) of PEBMA, 0.4 g (2 parts by mass) of DAEMA, 0.4 g (2 parts by mass) of IMADP, 59.8 g of acetone as a polymerization solvent and 0.2 g (1 part by mass) of 4,4'-azobis(4-cyanovaleric acid) as a polymerization initiator, were charged, and while shaking in a nitrogen atmosphere, polymerization was conducted at 65° C. for 20 hours, to obtain a pale yellow solution (polymer solution containing a fluorocopolymer (A-19)).

The copolymer composition of the fluoropolymer (A-19) was measured. As a result, it was confirmed to be a fluoropolymer having C6FMA units, PEBMA units, MPEG9MA units, DAEMA units and IMADP units in a molar ratio of 59:24:8:6:4 (mass ratio of 54:26:16:2:2).

Ex. 1

The fluoropolymer (A-1) obtained in Production Example 1 was dissolved in ethanol so that its concentration became to be a 0.05 mass %, to prepare a coating solution. The coating solution was dispensed in an amount of 2.2 mL on a microplate with 24 wells and left to stand for 3 days to evaporate the solvent, thereby to form a coating layer on the well surface.

Ex. 2 to 19

A coating solution was prepared in the same manner as in Ex. 1 except that a polymer shown in Table 3 was used instead of the fluoropolymer (A-1). Further, by using the coating solution, in the same manner as in Ex. 1, a coating layer was formed on the well surface of a microplate with 24 wells.

Ex. 20 to 23

A coating solution was prepared in the same manner as in Ex. 1 except that a fluoropolymer shown in Table 3 was used instead of the fluoropolymer (A-1). Further, by using the coating liquid, in the same manner as in Ex. 1, a coating layer was formed on the well surface of a microplate with 24 wells.

Ex. 24 to 26

To a solution prepared by dissolving the fluoropolymer (A-16) obtained in Production Example 20 in AC6000 (manufactured by Asahi Glass Company, Limited) so that its concentration became to be 0.05 mass %, a cross-linking agent was added to prepare a coating solution. As the cross-linking agent, to 28 g of the above solution, 0.1 mg of hexamethylene diisocyanate in Ex. 24, 0.13 mg of isophorone diisocyanate in Ex. 25, and 0.1 mg of TLA-100 (manufactured by Asahi Kasei Corporation) in Ex. 26, were added. By using such a coating solution, in the same manner as in Ex. 1, a coating layer was formed on the well surface of a microplate with 24 wells.

The type, fluorine atom content and proportion P of the fluoropolymer contained in the coating solution in each Ex. as well as the evaluation results of the water-insolubility and protein non-adherent properties, are shown in Table 3.

TABLE 3

| | | Fluoropolymer | | | Protein | | | Durability of coating layer | | |
|---|---|---|---|---|---|---|---|---|---|---|
| | | Fluorine atom content [mass %] | Proportion P [%] | Water insolubility | non-adherent adsorption rate Q [%] | Cell non-adhesion TIG-3 cells | HepG2 cells | Adsorption rate Q (after immersion) [%] | Increase in adsorption rate Q [%] | Evaluation result |
| Ex. | Type | | | | | | | | | |
| 1 | A-1 | 30.6 | 1.5 | o | 0.033 | o | o | 0.035 | 6.06 | Δ |
| 2 | A-2 | 28.8 | 1.7 | o | 0.079 | o | o | | | |
| 3 | A-3 | 16.0 | 4.5 | o | 0 | o | o | | | |
| 4 | X-1 | 11.0 | 7.4 | x | — | — | — | | | |
| 5 | X-2 | 33.9 | 0 | o | 0.3 | o | o | | | |
| 6 | A-4 | 17.8 | 2.6 | o | 0.035 | o | o | | | |
| 7 | A-5 | 13.6 | 4.4 | o | 0.082 | o | o | | | |
| 8 | X-3 | 10.5 | 6.5 | x | — | — | — | | | |
| 9 | A-6 | 39.2 | 0.8 | o | 0.092 | o | o | | | |

TABLE 3-continued

| | | Fluoropolymer | | | Protein | | | Durability of coating layer | | |
| --- | --- | --- | --- | --- | --- | --- | --- | --- | --- | --- |
| Ex. | Type | Fluorine atom content [mass %] | Proportion P [%] | Water insolubility | non-adherent adsorption rate Q [%] | Cell non-adhesion TIG-3 cells | HepG2 cells | Adsorption rate Q (after immersion) [%] | Increase in adsorption rate Q [%] | Evaluation result |
| 10 | A-7 | 26.5 | 2.0 | ○ | 0.021 | ○ | ○ | | | |
| 11 | A-8 | 19.1 | 3.5 | ○ | 0 | ○ | ○ | | | |
| 12 | A-9 | 33.7 | 1.2 | ○ | 0.03 | ○ | ○ | | | |
| 13 | A-10 | 27.4 | 1.9 | ○ | 0.024 | ○ | ○ | | | |
| 14 | A-11 | 20.0 | 3.3 | ○ | 0 | ○ | ○ | | | |
| 15 | X-4 | 0 | Infinite | x | — | — | — | | | |
| 16 | A-12 | 50.3 | 0.2 | ○ | 0.037 | ○ | ○ | | | |
| 17 | A-13 | 44.6 | 0.5 | ○ | 0 | ○ | ○ | | | |
| 18 | A-14 | 40.0 | 0.7 | ○ | 0.014 | ○ | ○ | | | |
| 19 | A-15 | 23.8 | 1.3 | ○ | 0 | ○ | ○ | | | |
| 20 | A-16 | 11.8 | 3.4 | ○ | 0.099 | ○ | ○ | 0.117 | 18.18 | Δ |
| 21 | A-17 | 28.6 | 1.2 | ○ | 0.006 | ○ | ○ | | | |
| 22 | A-18 | 11.8 | 6.8 | x | — | — | — | | | |
| 23 | A-19 | 31.9 | 1.3 | ○ | 0.012 | ○ | ○ | 0.014 | 16.67 | Δ |
| 24 | A-16 | 11.8 | 3.4 | ○ | 0.015 | ○ | ○ | 0.016 | 6.67 | ○ |
| 25 | A-16 | 11.8 | 3.4 | ○ | 0.020 | ○ | ○ | 0.021 | 5.00 | ○ |
| 26 | A-16 | 11.8 | 3.4 | ○ | 0.025 | ○ | ○ | 0.025 | 0.00 | ○ |

As shown in Table 3, in Ex. 1 to 3, 6, 7, 9 to 14, 16 to 21 and 23, wherein a coating solution containing a fluoropolymer (A) which has units having a biocompatible group, and a proportion P of from 0.1 to 4.5%, was used, protein was less likely to be adsorbed on the surface, cells were less likely to be adhered to the surface, and the biocompatibility was excellent. Further, the fluoropolymer was hardly soluble in water and thus was excellent in water insolubility.

On the other hand, in Ex. 4, 8, 15 and 22, wherein a polymer having a proportion P exceeding 4.5% was used, the polymer was likely to be easily dissolved in water and thus was insufficient in water resistance. Further, in Ex. 5 wherein a polymer having a proportion P of less than 0.1% was used, protein was adsorbed on the surface, and further, cells were adhered to the surface, and thus the biocompatibility was insufficient.

Further, in Ex. 24 to 26 wherein a coating solution having a fluoropolymer (A) and a crosslinking agent used in combination was used, as compared to Ex, 1, 20 and 23 wherein a cross-linking agent was not used in combination, even after immersion in water of 37° C. for one week, the rate of increase in protein adsorption rate Q was kept to be small, and thus, the durability was excellent.

Production Example 24

1.48 g (5.0 mmol) of MPC, 1.73 g (4.0 mmol) of C6FMA and 0.25 g (1.0 mmol) of KBM-503 (trimethoxysilyl propyl methacrylate) were weighed into a 300 mL three-necked flask, and 0.346 g of AIBN as a polymerization initiator, and 13.8 g of ethanol (EtOH) as a polymerization solvent, were added. The molar ratio of MPC, C6FMA and KBM-503 was adjusted to be MPC/C6FMA/KBM-503=50/40/10, the total concentration of the monomers in the reaction solution was made to be 20 mass %, and the initiator concentration was made to be 1 mass %.

Inside of the flask was thoroughly purged with argon, and then sealed and heated for 16 hours at 75° C. to conduct a polymerization reaction. The reaction solution was cooled with ice and then dropwise added to diethyl ether to precipitate the polymer. The obtained polymer was sufficiently washed with diethyl ether and then dried under reduced pressure to obtain a white powdery fluoropolymer (A-20).

The copolymer composition of the obtained fluoropolymer (A-20) was measured by $^1$H-NMR and found to be MPC units/C6FMA units/KBM-503 units=50/40/10 (molar ratio).

Production Examples 25 to 27

Each polymer was obtained in the same manner as in Production Example 24 except that the charged ratio of monomers was changed as shown in Table 4.

TABLE 4

| | | Fluoropolymer | | | |
| --- | --- | --- | --- | --- | --- |
| Preparation Example | Charged ratio Molar ratio | Type | Copolymer composition Molar ratio | Fluorine atom content [mass %] | Tg (° C.) |
| 24 | MPC/C6FMA/ KBM-503 50/40/10 | A-20 | MPC/C6FMA/ KBM-503 50/40/10 | 28.3 | |
| 25 | MPC/C6FMA/ KBM-503 50/45/5 | A-21 | MPC/C6FMA/ KBM-503 50/45/5 | 31.2 | |
| 26 | MPC/C6FMA/ KBM-503 50/47/3 | A-22 | MPC/C6FMA/ KBM-503 50/47/3 | 32.3 | |
| 27 | MPC/C6FMA/ KBM-503 50/50/0 | A-23 | MPC/C6FMA/ KBM-503 50/50/0 | 34.0 | 147 |

Ex. 27

0.5 g of the fluoropolymer (A-20) was weighed into a 20 mL vial, and 0.078 g of a 0.1 mass % nitric acid aqueous solution and 9.42 g of ethanol (EtOH) as a hydrolysis solvent, were added, to bring the concentration of the fluoropolymer (A-20) in the reaction solution to be 5 mass %. That is, by taking the molecular weight per one unit of the fluoropolymer (A-20) to be, from the actually measured molar ratio at the time of the copolymerization, MPC molecular weight×0.5+C6FMA molecular weight×0.4+

KBM-503 molecular weight×0.1=345.34, the amount of water to be added to trimethoxysilyl groups was made to be 3 molar equivalents.

The vial was stirred for 20 hours by a mixing rotor at room temperature, and the concentration of the fluoropolymer (A-20) was diluted with ethanol (EtOH) to be 0.05 mass %, to obtain a coating solution. 3.3 mL of the coating solution was applied to a glass petri dish having a diameter of 35 mm. After the application, by a hot plate, condensation was conducted at 120° C. for 2 hours to form a coating layer.

Ex. 28 to 30

A coating layer was formed on the surface of a glass petri dish in the same manner as in Ex. 1 except that a polymer shown in Table 5 was used instead of the fluoropolymer (A-20).

The type, the fluorine atom content and the proportion P of the fluoropolymer contained in the coating solution of each Ex., as well as the evaluation results, are shown in Table 5.

TABLE 5

|  |  | Fluoropolymer | | | Protein | | | Durability of coating layer | |
| --- | --- | --- | --- | --- | --- | --- | --- | --- | --- |
|  |  | Fluorine atom |  |  | non-adherent | Cell non-adhesion | | Adsorption rate Q (after | Substrate |
| Ex. | Type | content [mass %] | Proportion P [%] | Water insolubility | adsorption rate Q [%] | TIG-3 cells | HepG2 cells | immersion) [%] | adhesion rate Z |
| 27 | A-20 | 28.3 | 1.5 | ○ | 0.077 |  |  | 0.081 | 1.1 |
| 28 | A-21 | 31.2 | 1.3 | ○ | 0.023 |  |  | 0.018 | 0.8 |
| 29 | A-22 | 32.3 | 1.3 | ○ | 0.010 |  |  | 0.016 | 1.5 |
| 30 | A-23 | 34.0 | 1.2 | ○ | 0.031 |  |  | 0.186 | 6.0 |

As shown in Table 5, in Ex. 27 to 30 wherein a coating solution containing a fluoropolymer (A) which has units having a biocompatible group and a proportion P of from 0.1 to 4.5 mass %, was used, protein was less likely to be adsorbed on the surface, cells were less likely to be adhered to the surface, and thus, the biocompatibility was excellent. Further, in Ex. 27 to 29 wherein a coating solution containing a fluoropolymer (A) which has units (m7) was used, as compared to Ex. 30 wherein a coating solution containing a fluoropolymer (A) which contains no units (m7) was used, the water-insolubility was further excellent.

INDUSTRIAL APPLICABILITY

The coating layer using the protein adhesion inhibitor of the present invention becomes a layer which is excellent in water resistance, from which coating components are less likely to be eluted, on which protein is less likely to be adsorbed and which is excellent in biocompatibility, and thus, is useful for coating of marine structures, medical devices, etc. and, for example, it is utilized in catheters, artificial organs, cell culture vessels, etc.

REFERENCE SYMBOLS

1: medical device, 2: device substrate, 3: coating layer, 4: bottom portion, 5: side portion

What is claimed is:

1. A protein adhesion inhibitor comprising a fluoropolymer having units having a biocompatible group, a fluorine atom content of from 5 to 60 mass % and a proportion P represented by the following formula of from 0.1 to 4.5%:

(Proportion P) =[(proportion (mass %) of units having a biocompatible group to all units of the fluoropolymer)/(fluorine atom content (mass %) of the fluoropolymer)] ×100%, wherein the fluoropolymer has units derived from a monomer represented by the following formula (m1), units derived from a monomer represented by the following formula (m4), and units derived from a monomer represented by the following formula (m5),

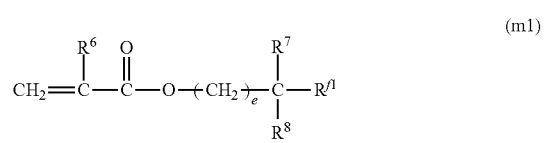
(m1)

-continued

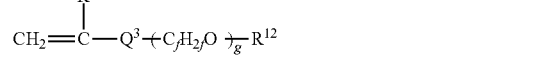
(m4)

and $$CH_2=CR^{14}-COO-Q^4-R^{15} \quad (m5),$$

wherein:
$R^6$ is a hydrogen atom, a chlorine atom or a methyl group,
e is an integer of from 0 to 3,
$R^7$ and $R^8$ are each independently a hydrogen atom, a fluorine atom or a trifluoromethyl group,
$R^{f1}$ is a $C_{1\text{-}20}$ perfluoroalkyl group,
$R^{11}$ is a hydrogen atom, a chlorine atom or a methyl group,
$Q^3$ is —COO— or —COO(CH$_2$)$_h$—NHCOO—, wherein h is an integer of from 1 to 4,
$R^{12}$ is a hydrogen atom or 13 (CH$_2$)$_i$—R$^{13}$, wherein R$^{13}$ is a $C_{1\text{-}8}$ alkoxy group, a hydrogen atom, a fluorine atom, a trifluoromethyl group or a cyano group, and i is an integer of from 1 to 25,
f is an integer of from 1 to 10,
g is an integer of from 1 to 100,
$R^{14}$ is a hydrogen atom, a chlorine atom or a methyl group,
$R^{15}$ is a $C_{1\text{-}8}$ alkoxy group, a hydrogen atom, a hydroxy group or a cyano group, and
$Q^4$ is a single bond, a $C_{1\text{-}20}$ alkylene group, a $C_{1\text{-}12}$ polyfluoroalkylene group or —CF$_2$—(OCF$_2$CF$_2$)$_y$—OCF$_2$— wherein y is an integer of from 1 to 6, and wherein the units derived from the monomer represented by the formula (m1) are present in the fluoropolymer in a range of 19 to 28 mass %, based on the mass of the fluoropolymer.

2. The protein adhesion inhibitor according to claim 1, wherein the monomer represented by the formula (m1) comprises a monomer having the following formula:

$CH_2\!=\!CHCOO(CH_2)_2(CF_2)_5CF_3$.

3. The protein adhesion inhibitor according to claim 1, wherein the monomer represented by the formula (m4) comprises polyethylene glycol monoacrylate having an average EO number of 9.

4. The protein adhesion inhibitor according to claim 1, wherein the monomer represented by the formula (m5) comprises a monomer having the following formula:

$CH_2\!=\!CHCOOCH_2CH(C_2H_5)CH_2CH_2CH_2CH_3$.

5. The protein adhesion inhibitor according to claim 1, wherein:

the monomer represented by the formula (m1) comprises a monomer having the following formula:

$CH_2\!=\!CHCOO(CH_2)_2(CF_2)_5CF_3$;

the monomer represented by the formula (m4) comprises polyethylene glycol monoacrylate having an average EO number of 9; and the monomer represented by the formula (m5) comprises a monomer having the following formula:

$CH_2\!=\!CHCOOCH_2CH(C_2H_5)CH_2CH_2CH_2CH_3$.

6. A coating solution comprising the protein adhesion inhibitor according to claim 1 and a solvent.

7. The coating solution according to claim 6, further comprising a crosslinking agent.

8. The coating solution according to claim 7, wherein the fluoropolymer in the protein adhesion inhibitor has a hydroxy group, and the crosslinking agent is a polyfunctional isocyanate compound.

9. A medical device comprising a device substrate and a coating layer formed on the device substrate, wherein the coating layer is a layer formed from the protein adhesion inhibitor according to claim 1.

10. The medical device according to claim 9, which is a cell culture vessel.

11. A method for producing a medical device, which comprises:

applying the coating solution according to claim 7 onto a device substrate and removing the solvent derived from the coating solution to obtain a medical device having a coating layer formed on the device substrate.

12. A protein adhesion inhibitor comprising a fluoropolymer having units having a biocompatible group, a fluorine atom content of from 5 to 60 mass % and a proportion P represented by the following formula of from 0.1 to 4.5%:

(Proportion $P$) =[(proportion (mass %) of units having a biocompatible group to all units of the fluoropolymer)/(fluorine atom content (mass %) of the fluoropolymer)]×100%, wherein the fluoropolymer has a segment (I) comprising units (m6) derived from a monomer represented by the following formula (m6), and a segment (II) comprising a molecular chain derived from a polymeric azo initiator having a structure represented by the following formula (6):

(m6)

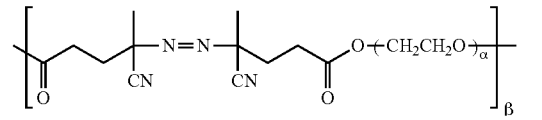

(6)

wherein:
R$^{16}$ is a hydrogen atom, a C$_{1-4}$ alkyl group or a halogen atom,
Q$^5$ is a single bond or a divalent organic group,
R$^{17}$ is a C$_{1-6}$ polyfluoroalkyl group which may have an etheric oxygen atom between carbon atoms,
α is an integer of from 5 to 300, and
β is an integer of from 1 to 20.

* * * * *